(12) United States Patent
Ahdieh

(10) Patent No.: US 8,808,737 B2
(45) Date of Patent: Aug. 19, 2014

(54) METHOD OF TREATING PAIN UTILIZING CONTROLLED RELEASE OXYMORPHONE PHARMACEUTICAL COMPOSITIONS AND INSTRUCTION ON DOSING FOR RENAL IMPAIRMENT

(75) Inventor: Harry Ahdieh, Lincoln University, PA (US)

(73) Assignee: Endo Pharmaceuticals Inc., Malvern, PA (US)

( * ) Notice: Subject to any disclaimer, the term of this patent is extended or adjusted under 35 U.S.C. 154(b) by 0 days.

(21) Appl. No.: 12/716,973

(22) Filed: Mar. 3, 2010

(65) Prior Publication Data

US 2010/0151027 A1 Jun. 17, 2010

Related U.S. Application Data

(63) Continuation of application No. 11/766,740, filed on Jun. 21, 2007, now abandoned.

(51) Int. Cl.
*A61K 9/20* (2006.01)
*A61K 9/14* (2006.01)
*A61K 31/44* (2006.01)

(52) U.S. Cl.
USPC ............................. 424/464; 424/484; 514/282

(58) Field of Classification Search
USPC .................................. 424/464, 484; 514/282
See application file for complete search history.

(56) References Cited

U.S. PATENT DOCUMENTS

| | | |
|---|---|---|
| 4,366,159 A | 12/1982 | Magruder |
| 4,711,782 A | 12/1987 | Okada et al. |
| 5,415,871 A | 5/1995 | Pankhania et al. |
| 5,478,577 A | 12/1995 | Sackler et al. |
| 6,143,322 A | 11/2000 | Sackler et al. |
| 6,228,398 B1 | 5/2001 | Devane et al. |
| 6,245,351 B1 | 6/2001 | Nara et al. |
| 6,294,195 B1 | 9/2001 | Oshlack et al. |
| 6,309,668 B1 | 10/2001 | Bastin et al. |
| 2001/0008639 A1 | 7/2001 | Oshlack et al. |
| 2002/0032581 A1 | 3/2002 | Reitberg |
| 2003/0091635 A1 | 5/2003 | Baichwal et al. |
| 2003/0129230 A1 | 7/2003 | Baichwal et al. |
| 2003/0129234 A1 | 7/2003 | Baichwal et al. |
| 2003/0157167 A1 | 8/2003 | Kao et al. |

FOREIGN PATENT DOCUMENTS

| | | |
|---|---|---|
| EP | 360562 B2 | 3/1990 |
| WO | WO-93/17673 A1 | 9/1993 |
| WO | WO-98/00143 A1 | 1/1998 |
| WO | WO-99/01111 A1 | 1/1999 |
| WO | WO-01/08661 A2 | 2/2001 |
| WO | WO-01/32148 A1 | 5/2001 |

OTHER PUBLICATIONS

Prommer, E., Oxymorphone: a review, Support Care Center (2006) 14:109-115 (published on line Nov. 30, 2005).*

* cited by examiner

*Primary Examiner* — Aradhana Sasan
(74) *Attorney, Agent, or Firm* — Mayer Brown LLP

(57) ABSTRACT

The invention pertains to a method of using oxymorphone in the treatment of pain by providing a patient with an oxymorphone dosage form and informing the patient or prescribing physician that the bioavailability of oxymorphone is increased in patients with renal impairment.

6 Claims, 16 Drawing Sheets

METHOD OF TREATING PAIN UTILIZING CONTROLLED RELEASE OXYMORPHONE PHARMACEUTICAL COMPOSITIONS AND INSTRUCTION ON DOSING FOR RENAL IMPAIRMENT

BACKGROUND OF THE INVENTION

Pain is the most frequently reported symptom and it is a common clinical problem which confronts the clinician. Many millions of people in the USA suffer from severe pain that, according to numerous recent reports, is chronically undertreated or inappropriately managed. The clinical usefulness of the analgesic properties of opioids has been recognized for centuries, and morphine and its derivatives have been widely employed for analgesia for decades in a variety of clinical pain states.

Oxymorphone HCl (14-hydroxydihydromorphinone hydrochloride) is a semi-synthetic phenanthrene-derivative opioid agonist, widely used in the treatment of acute and chronic pain, with analgesic efficacy comparable to other opioid analgesics. Oxymorphone is currently marketed as an injection (1 mg/ml in 1 ml ampules; 1.5 mg/ml in 1 ml ampules; 1.5 mg/ml in 10 ml multiple dose vials) for intramuscular, subcutaneous, and intravenous administration, and as 5 mg rectal suppositories. At one time, 2 mg, 5 mg and 10 mg oral immediate release (IR) tablet formulations of oxymorphone HCl were marketed. Oxymorphone HCl is metabolized principally in the liver and undergoes conjugation with glucuronic acid and reduction to 6-alpha- and beta-hydroxy epimers.

An important goal of analgesic therapy is to achieve continuous relief of chronic pain. Regular administration of an analgesic is generally required to ensure that the next dose is given before the effects of the previous dose have worn off. Compliance with opioids increases as the required dosing frequency decreases. Non-compliance results in suboptimal pain control and poor quality of life outcomes. (Ferrell B et al. Effects of controlled-release morphine on quality of life for cancer pain. *Oncol. Nur. Forum* 1989; 4:521-26). Scheduled, rather than "as needed" administration of opioids is currently recommended in guidelines for their use in chronic non-malignant pain. Unfortunately, evidence from prior clinical trials and clinical experience suggests that the short duration of action of immediate release oxymorphone would necessitate administration every 4-6 hours in order to maintain optimal levels of analgesia in chronic pain. A controlled release formulation which would allow less frequent dosing of oxymorphone would be useful in pain management.

For instance, a controlled release formulation of morphine has been demonstrated to provide patients fewer interruptions in sleep, reduced dependence on caregivers, improved compliance, enhanced quality of life outcomes, and increased control over the management of pain. In addition, the controlled release formulation of morphine was reported to provide more constant plasma concentration and clinical effects, less frequent peak to trough fluctuations, reduced dosing frequency, and possibly fewer side effects. (Thirlwell M P et al., Pharmacokinetics and clinical efficacy of oral morphine solution and controlled-release morphine tablets in cancer patients. *Cancer* 1989; 63:2275-83; Goughnour B R et al., Analgesic response to single and multiple doses of controlled-release morphine tablets and morphine oral solution in cancer patients. *Cancer* 1989; 63:2294-97; Ferrell B. et al., Effects of controlled-release morphine on quality of life for cancer pain. *Oncol. Nur. Forum* 1989; 4:521-26.

There are two factors associated with the metabolism of some drugs that may present problems for their use in controlled release systems. One is the ability of the drug to induce or inhibit enzyme synthesis, which may result in a fluctuating drug blood plasma level with chronic dosing. The other is a fluctuating drug blood level due to intestinal (or other tissue) metabolism or through a hepatic first-pass effect.

Oxymorphone is metabolized principally in the liver, resulting in an oral bioavailability of about 10%. Evidence from clinical experience suggests that the short duration of action of immediate release oxymorphone necessitates a four hour dosing schedule to maintain optimal levels of analgesia. It would be useful to clinicians and patients alike to have controlled release dosage forms of oxymorphone to use to treat pain and a method of treating pain using the dosage forms.

Diseases of the kidney can cause impaired kidney function. Chronic renal failure in particular can be caused by any number of sources, including diabetes and high blood pressure, which are two of the most common causes according to the National Kidney Foundation. Impaired kidney function results in a potential build up of substances that are typically filtered out by the kidneys, such as waste products as well as some drugs.

SUMMARY OF THE INVENTION

One aspect of the invention is a method of using oxymorphone in the treatment of pain comprising providing a patient with a therapeutically effective amount of oxymorphone and informing the patient or the patient's prescribing physician that the bioavailability of oxymorphone is increased in patients with renal impairment.

Another aspect of the invention provides a method of using oxymorphone in the treatment of pain in a patient having renal impairment in need thereof comprising providing a patient having renal impairment with a therapeutically effective amount of an oral dosage form of oxymorphone, informing the patient or the patient's prescribing physician that the bioavailability of oxymorphone is increased in patients with renal impairment, and orally administering the dosage form of oxymorphone to the patient.

A further aspect of the invention provides a method of using oxymorphone in the treatment of pain in a patient having moderate or severe renal impairment in need thereof comprising providing a patient having moderate or severe renal impairment with a therapeutically effective amount of a controlled release oral dosage form of oxymorphone, informing the patient or the patient's prescribing physician that the bioavailability of oxymorphone is increased in patients with renal impairment, and orally administering the composition to the patient, wherein the log transformed AUC of oxymorphone is about 1.05 to about 2.45 times greater than the log transformed AUC of a healthy patient if the healthy patient were to be administered the same dose.

DETAILED DESCRIPTION OF THE INVENTION

Figure 1:
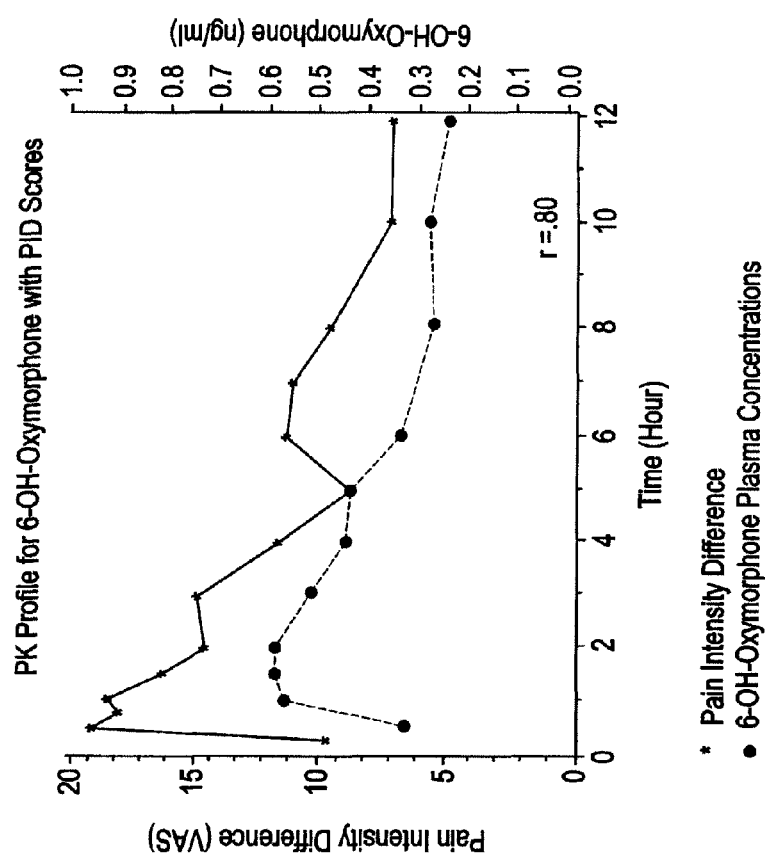
FIG. 1 is a pharmacokinetic profile for 6-hydroxy oxymorphone with PID scores.

The present invention provides methods using oxymorphone in the treatment of pain. In one aspect of the invention the method may involve steps of providing a patient with a therapeutically effective amount of oxymorphone and informing the patient or the patient's prescribing physician that the bioavailability of oxymorphone is increased in patients with renal impairment.

Among the controlled (or extended) release, as well as immediate release, pharmaceutical compounds comprising oxymorphone that may be used in the methods of this invention is Opana®, which upon its approval on Jun. 22, 2006 became the first-ever controlled release oxymorphone formulation to be approved by the United States Food and Drug Administration (FDA). Opana® is available in both immediate release and controlled or extended release dosage forms. The approved labels of Opana® are incorporated herein by reference to the extent permitted by law.

The present invention also provides methods for alleviating pain for 12 to 24 hours using a single dose of a pharmaceutical composition by producing a blood plasma level of oxymorphone and/or 6-OH oxymorphone of at least a minimum value for at least 12 hours or more. As used herein, the terms "6-OH oxymorphone" and "6-hydroxy oxymorphone" are interchangeable and refer to the analog of oxymorphone having an alcohol (hydroxy) moiety that replaces the carboxy moiety found on oxymorphone at the 6-position.

To overcome the difficulties associated with a 4-6 hourly dosing frequency of oxymorphone, this invention provides an oxymorphone controlled release oral solid dosage form, comprising a therapeutically effective amount of oxymorphone or a pharmaceutically acceptable salt of oxymorphone. It has been found that the decreased rate of release of oxymorphone from the oral controlled release formulation of this invention does not substantially decrease the bioavailability of the drug as compared to the same dose of a solution of oxymorphone administered orally. The bioavailability is sufficiently high and the release rate is such that a sufficient plasma level of oxymorphone and/or 6-OH oxymorphone is maintained to allow the controlled release dosage to be used to treat patients suffering moderate to severe pain with once or twice daily dosing. The dosing form of the present invention can also be used with thrice daily dosing.

It is critical when considering the present invention that the difference between a controlled release tablet and an immediate release formulation be fully understood. In classical terms, an immediate release formulation releases at least 80% of its active pharmaceutical ingredient within 30 minutes. With reference to the present invention, the definition of an immediate release formulation will be broadened further to include a formulation which releases more than about 80% of its active pharmaceutical ingredient within 60 minutes in a standard USP Paddle Method dissolution test at 50 rpm in 500 ml media having a pH of between 1.2 and 6.8 at 37° C. "Controlled release" formulations, as referred to herein, will then encompass any formulations which release no more than about 80% of their active pharmaceutical ingredients within 60 minutes under the same conditions.

The controlled release dosage form of this invention exhibits a dissolution rate in vitro, when measured by USP Paddle Method at 50 rpm in 500 ml media having a pH between 1.2 and 6.8 at 37° C., of about 15% to about 50% by weight oxymorphone released after 1 hour, about 45% to about 80% by weight oxymorphone released after 4 hours, and at least about 80% by weight oxymorphone released after 10 hours.

When administered orally to humans, an effective controlled release dosage form of oxymorphone should exhibit the following in vivo characteristics: (a) peak plasma level of oxymorphone occurs within about 1 to about 8 hours after administration; (b) peak plasma level of 6-OH oxymorphone occurs within about 1 to about 8 hours after administration; (c) duration of analgesic effect is through about 8 to about 24 hours after administration; (d) relative oxymorphone bioavailability is in the range of about 0.5 to about 1.5 compared to an orally-administered aqueous solution of oxymorphone; and (e) the ratio of the area under the curve of blood plasma level vs. time for 6-OH oxymorphone compared to oxymorphone is in the range of about 0.5 to about 1.5. Of course, there is variation of these parameters among subjects, depending on the size and weight of the individual subject, the subject's age, individual metabolism differences, and other factors. Indeed, the parameters may vary in an individual from day to day. Accordingly, the parameters set forth above are intended to be mean values from a sufficiently large study so as to minimize the effect of individual variation in arriving at the values. A convenient method for arriving at such values is by conducting a study in accordance with standard FDA procedures such as those employed in producing results for use in a new drug application (or abbreviated new drug application) before the FDA. Any reference to mean values herein, in conjunction with desired results, refer to results from such a study, or some comparable study. Reference to mean values reported herein for studies actually conducted are arrived at using standard statistical methods as would be employed by one skilled in the art of pharmaceutical formulation and testing for regulatory approval.

In one specific embodiment of the controlled release matrix form of the invention, the oxymorphone or salt of oxymorphone is dispersed in a controlled release delivery system that comprises a hydrophilic material which, upon exposure to gastrointestinal fluid, forms a gel matrix that releases oxymorphone at a controlled rate. The rate of release of oxymorphone from the matrix depends on the drug's partition coefficient between components of the matrix and the aqueous phase within the gastrointestinal tract. In a preferred form of this embodiment, the hydrophilic material of the controlled release delivery system comprises a mixture of a heteropolysaccharide gum and an agent capable of cross-linking the heteropolysaccharide in presence of gastrointestinal fluid. The controlled release delivery system may also comprise a water-soluble pharmaceutical diluent mixed with the hydrophilic material. Preferably, the cross-linking agent is a homopolysaccharide gum and the inert pharmaceutical diluent is a monosaccharide, a disaccharide, or a polyhydric alcohol, or a mixture thereof.

In a specific preferred embodiment, the appropriate blood plasma levels of oxymorphone and 6-hydroxy oxymorphone are achieved using oxymorphone in the form of oxymorphone hydrochloride, wherein the weight ratio of heteropolysaccharide to homopolysaccharide is in the range of about 1:3 to about 3:1, the weight ratio of heteropolysaccharide to diluent is in the range of about 1:8 to about 8:1, and the weight ratio of heteropolysaccharide to oxymorphone hydrochloride is in the range of about 10:1 to about 1:10. A preferred heteropolysaccharide is xanthan gum and a preferred homopolysaccharide is locust bean gum. The dosage form also comprises a cationic cross-linking agent and a hydrophobic polymer. In the preferred embodiment, the dosage form is a tablet containing about 5 mg to about 80 mg of oxymorphone hydrochloride. In a most preferred embodiment, the tablet contains about 20 mg oxymorphone hydrochloride.

The invention includes a method which comprises achieving appropriate blood plasma levels of drug while providing extended pain relief by administering one to three times per day to a patient suffering moderate to severe, acute or chronic pain, an oxymorphone controlled release oral solid dosage form of the invention in an amount sufficient to alleviate the pain for a period of about 8 hours to about 24 hours. This type and intensity of pain is often associated with cancer, autoimmune diseases, infections, surgical and accidental traumas and osteoarthritis.

The invention also includes a method of making an oxymorphone controlled release oral solid dosage form of the invention which comprises mixing particles of oxymorphone or a pharmaceutically acceptable salt of oxymorphone with granules comprising the controlled release delivery system, preferably followed by directly compressing the mixture to form tablets.

Pharmaceutically acceptable salts of oxymorphone which can be used in this invention include salts with the inorganic and organic acids which are commonly used to produce non-toxic salts of medicinal agents. Illustrative examples would be those salts formed by mixing oxymorphone with hydrochloric, sulfuric, nitric, phosphoric, phosphorous, hydrobromic, maleric, malic, ascorbic, citric or tartaric, pamoic, lauric, stearic, palmitic, oleic, myristic, lauryl sulfuric, naphthalenesulfonic, linoleic or linolenic acid, and the like. The hydrochloride salt is preferred.

It has now been found that 6-OH oxymorphone, which is one of the metabolites of oxymorphone, may play a role in alleviating pain. When oxymorphone is ingested, part of the dosage gets into the bloodstream to provide pain relief, while another part is metabolized to 6-OH oxymorphone. This metabolite then enters the bloodstream to provide further pain relief. Thus it is believed that both the oxymorphone and 6-hydroxyoxymorphone levels are important to pain relief.

Figure 2:
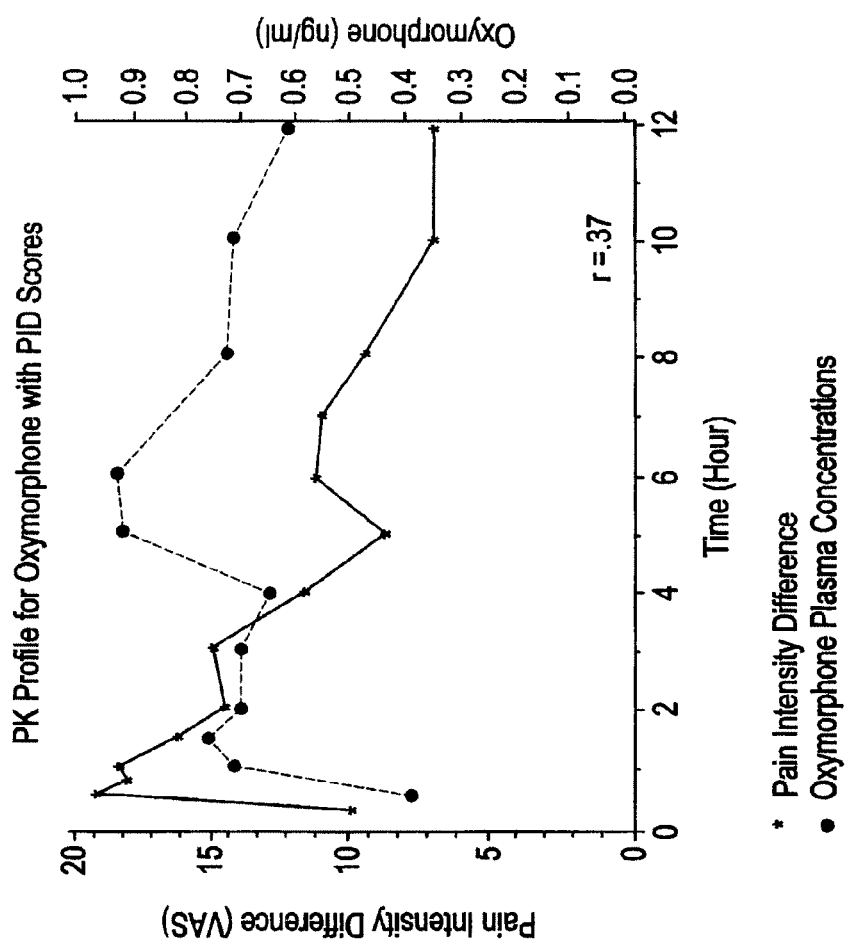
FIG. 2 is a pharmacokinetic profile for oxymorphone with PID scores.
Figure 3:
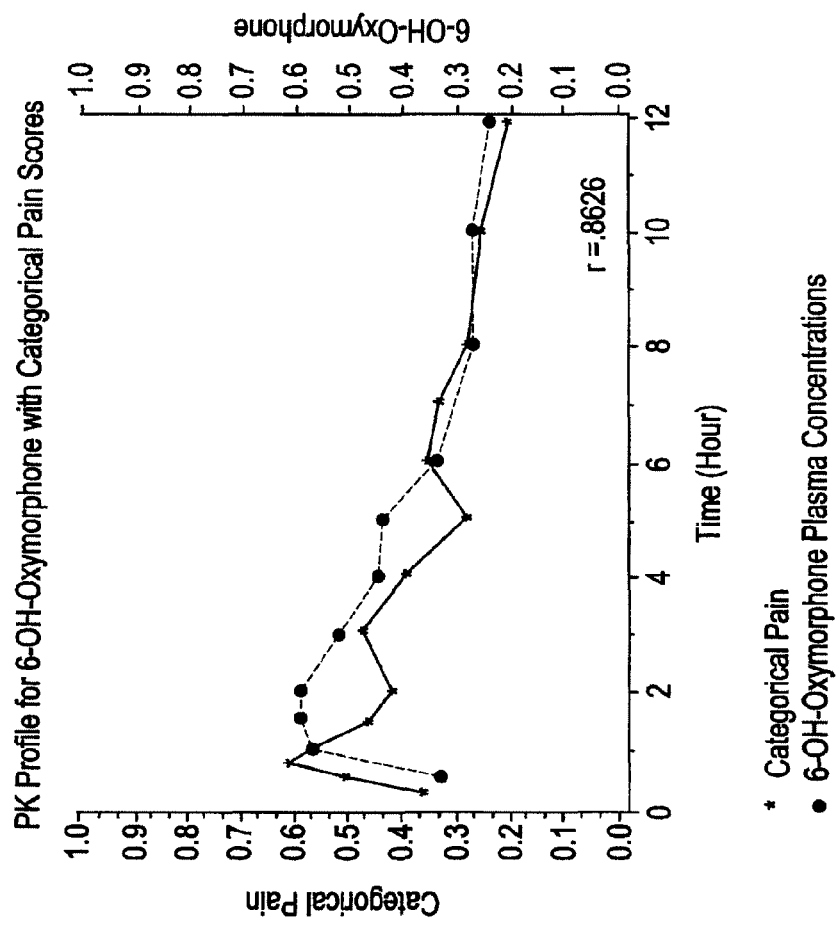
FIG. 3 is a pharmacokinetic profile for 6-hydroxy oxymorphone with categorical pain scores.
Figure 4:
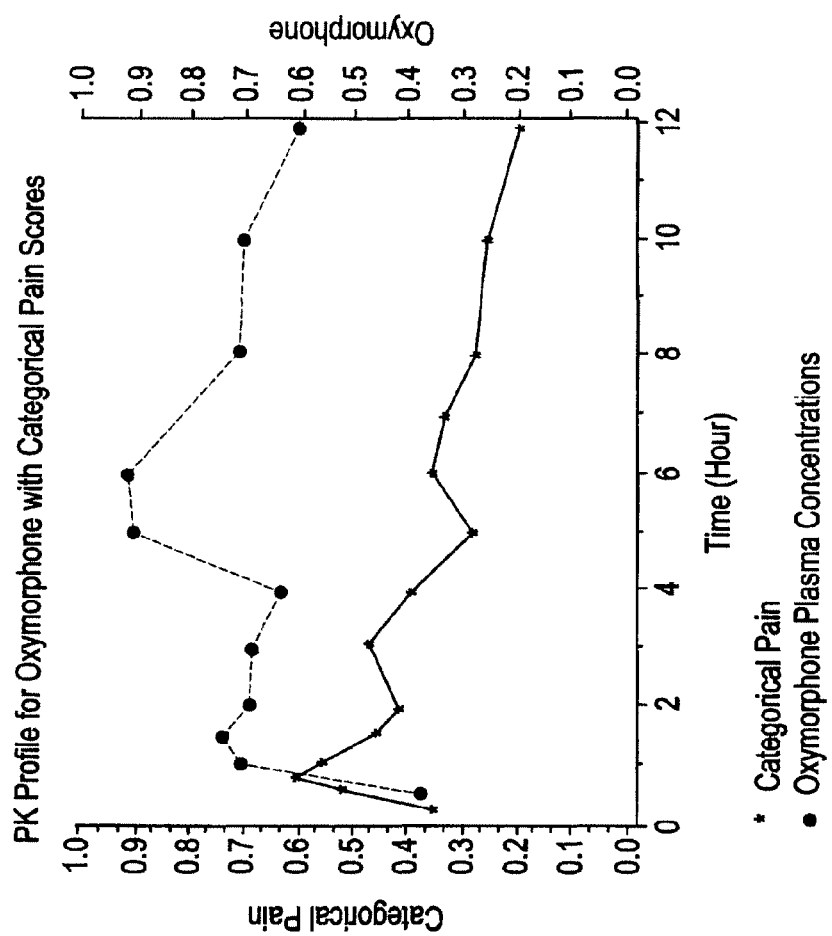
FIG. 4 is a pharmacokinetic profile for oxymorphone with categorical pain scores.

The effectiveness of oxymorphone and 6-hydroxyoxymorphone at relieving pain and the pharmacokinetics of a single dose of oxymorphone were studied. The blood plasma levels of both oxymorphone and 6-hydroxyoxymorphone were measured in patients after a single dose of oxymorphone was administered. Similarly, the pain levels in patients were measured after a single administration of oxymorphone to determine the effective duration of pain relief from a single dose. FIGS. 1-2 show the results of these tests, comparing pain levels to oxymorphone and 6-hydroxy oxymorphone levels.

For these tests, pain was measured using a Visual Analog Scale (VAS) or a Categorical Scale. The VAS scales consisted of a horizontal line, 100 mm in length. The left-hand end of the scale (0 mm) was marked with the descriptor "No Pain" and the right-hand end of the scale (100 mm) was marked with the descriptor "Extreme Pain". Patients indicated their level of pain by making a vertical mark on the line. The VAS score was equal to the distance (in mm) from the left-hand end of the scale to the patient's mark. For the categorical scale, patients completed the following statement, "My pain at this time is" using the scale None=0, Mild=1, Moderate=2, or Severe=3.

As can be seen from these figures, there is a correlation between pain relief and both oxymorphone and 6-hydroxyoxymorphone levels. As the blood plasma levels of oxymorphone and 6-hydroxyoxymorphone increase, pain decreases (and pain intensity difference and pain relief increases). Thus, to the patient, it is the level of oxymorphone and 6-hydroxyoxymorphone in the blood plasma which is most important. Further it is these levels which dictate the efficacy of the dosage form. A dosage form which maintains a sufficiently high level of oxymorphone or 6-hydroxyoxymorphone for a longer period need not be administered frequently. Such a result is accomplished by embodiments of the present invention.

The oxymorphone controlled release oral solid dosage form of this invention can be made using any of several different techniques for producing controlled release oral solid dosage forms of opioid analgesics.

In one embodiment, a core comprising oxymorphone or oxymorphone salt is coated with a controlled release film which comprises a water insoluble material and which upon exposure to gastrointestinal fluid releases oxymorphone from the core at a controlled rate. In a second embodiment, the oxymorphone or oxymorphone salt is dispersed in a controlled release delivery system that comprises a hydrophilic material which upon exposure to gastrointestinal fluid forms a gel matrix that releases oxymorphone at a controlled rate. A third embodiment is a combination of the first two: a controlled release matrix coated with a controlled release film. In a fourth embodiment the oxymorphone is incorporated into an osmotic pump. In any of these embodiments, the dosage form can be a tablet, a plurality of granules in a capsule, or other suitable form, and can contain lubricants, colorants, diluents, and other conventional ingredients.

Osmotic Pump

An osmotic pump comprises a shell defining an interior compartment and having an outlet passing through the shell. The interior compartment contains the active pharmaceutical ingredient. Generally the active pharmaceutical ingredient is mixed with excipients or other compositions such as a polyalkylene. The shell is generally made, at least in part, from a material (such as cellulose acetate) permeable to the liquid of the environment where the pump will be used, usually stomach acid. Once ingested, the pump operates when liquid diffuses through the shell of the pump. The liquid dissolves the composition to produce a saturated situation. As more liquid diffuses into the pump, the saturated solution containing the pharmaceutical is expelled from the pump through the outlet. This produces a nearly constant release of active ingredient, in the present case, oxymorphone.

Controlled Release Coating

In this embodiment, a core comprising oxymorphone or oxymorphone salt is coated with a controlled release film which comprises a water insoluble material. The film can be applied by spraying an aqueous dispersion of the water insoluble material onto the core. Suitable water insoluble materials include alkyl celluloses, acrylic polymers, waxes (alone or in admixture with fatty alcohols), shellac and zein. The aqueous dispersions of alkyl celluloses and acrylic polymers preferably contain a plasticizer such as triethyl citrate, dibutyl phthalate, propylene glycol, and polyethylene glycol. The film coat can contain a water-soluble material such as polyvinylpyrrolidone (PVP) or hydroxypropylmethylcellulose (HPMC).

The core can be a granule made, for example, by wet granulation of mixed powders of oxymorphone or oxymorphone salt and a binding agent such as HPMC, or by coating an inert bead with oxymorphone or oxymorphone salt and a binding agent such as HPMC, or by spheronising mixed powders of oxymorphone or oxymorphone salt and a spheronising agent such as microcrystalline cellulose. The core can be a tablet made by compressing such granules or by compressing a powder comprising oxymorphone or oxymorphone salt.

The in vitro and in vivo release characteristics of this controlled release dosage form can be modified by using mixtures of different water insoluble and water soluble materials, using different plasticizers, varying the thickness of the controlled release film, including release-modifying agents in the coating, or by providing passageways through the coating.

Controlled Release Matrix

It is important in the present invention that appropriate blood plasma levels of oxymorphone and 6-hydroxy oxymorphone be achieved and maintained for sufficient time to provide pain relief to a patient for a period of 12 to 24 hours. The preferred composition for achieving and maintaining the proper blood plasma levels is a controlled-release matrix. In this embodiment, the oxymorphone or oxymorphone salt is dispersed in a controlled release delivery system that comprises a hydrophilic material (gelling agent) which upon exposure to gastrointestinal fluid forms a gel matrix that releases oxymorphone at a controlled rate. Such hydrophilic materials include gums, cellulose ethers, acrylic resins, and protein-derived materials. Suitable cellulose ethers include hydroxyalkyl celluloses and carboxyalkyl celluloses, especially hydroxyethyl cellulose (HEC), hydroxypropyl cellulose (HPC), HPMC, and carboxy methylcellulose (CMC). Suitable acrylic resins include polymers and copolymers of acrylic acid, methacrylic acid, methyl acrylate and methyl methacrylate. Suitable gums include heteropolysaccharide and homopolysaccharide gums, e.g., xanthan, tragacanth, acacia, karaya, alginates, agar, guar, hydroxypropyl guar, carrageenan, and locust bean gums.

Preferably, the controlled release tablet of the present invention is formed from (I) a hydrophilic material comprising (a) a heteropolysaccharide; or (b) a heteropolysaccharide and a cross-linking agent capable of cross-linking said heteropolysaccharide; or (c) a mixture of (a), (b) and a polysaccharide gum; and (II) an inert pharmaceutical filler comprising up to about 80% by weight of the tablet; and (III) oxymorphone.

The term "heteropolysaccharide" as used herein is defined as a water-soluble polysaccharide containing two or more kinds of sugar units, the heteropolysaccharide having a branched or helical configuration, and having excellent water-wicking properties and immense thickening properties.

A preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The cross linking agents used in the controlled release embodiment of the present invention which are capable of cross-linking with the heteropolysaccharide include homopolysaccharide gums such as the galactomannans, i.e., polysaccharides which are composed solely of mannose and galactose. Galactomannans which have higher proportions of unsubstituted mannose regions have been found to achieve more interaction with the heteropolysaccharide. Locust bean gum, which has a higher ratio of mannose to the galactose, is especially preferred as compared to other galactomannans such as guar and hydroxypropyl guar.

Preferably, the ratio of heteropolysaccharide to homopolysaccharide is in the range of about 1:9 to about 9:1, preferably about 1:3 to about 3:1. Most preferably, the ratio of xanthan gum to polysaccharide material (i.e., locust bean gum, etc.) is preferably about 1:1.

In addition to the hydrophilic material, the controlled release delivery system can also contain an inert pharmaceutical diluent such as a monosaccharide, a disaccharide, a polyhydric alcohol and mixtures thereof. The ratio of diluent to hydrophilic matrix-forming material is generally in the range of about 1:3 to about 3:1.

The controlled release properties of the controlled release embodiment of the present invention may be optimized when the ratio of heteropolysaccharide gum to homopolysaccharide material is about 1:1, although heteropolysaccharide gum in an amount of from about 20 to about 80% or more by weight of the heterodisperse polysaccharide material provides an acceptable slow release product. The combination of any homopolysaccharide gums known to produce a synergistic effect when exposed to aqueous solutions may be used in accordance with the present invention. It is also possible that the type of synergism which is present with regard to the gum combination of the present invention could also occur between two homogeneous or two heteropolysaccharides. Other acceptable gelling agents which may be used in the present invention include those gelling agents well-known in the art. Examples include vegetable gums such as alginates, carrageenan, pectin, guar gum, xanthan gum, modified starch, hydroxypropylmethylcellulose, methylcellulose, and other cellulosic materials such as sodium carboxymethylcellulose and hydroxypropyl cellulose. This list is not meant to be exclusive.

The combination of xanthan gum with locust bean gum with or without the other homopolysaccharide gums is an especially preferred gelling agent. The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract.

The inert filler of the sustained release excipient preferably comprises a pharmaceutically acceptable saccharide, including a monosaccharide, a disaccharide, or a polyhydric alcohol, and/or mixtures of any of the foregoing. Examples of suitable inert pharmaceutical fillers include sucrose, dextrose, lactose, microcrystalline cellulose, fructose, xylitol, sorbitol, mixtures thereof and the like. However, it is preferred that a soluble pharmaceutical filler such as lactose, dextrose, sucrose, or mixtures thereof be used.

The cationic cross-linking agent which is optionally used in conjunction with the controlled release embodiment of the present invention may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable cationic cross-linking agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred cationic cross-linking agents are bivalent. Particularly preferred salts are calcium sulfate and sodium chloride. The cationic cross-linking agents of the present invention are added in an amount effective to obtain a desirable increased gel strength due to the cross-linking of the gelling agent (e.g., the heteropolysaccharide and homopolysaccharide gums). In preferred embodiments, the cationic cross-linking agent is included in the sustained release excipient of the present invention in an amount from about 1 to about 20% by weight of the sustained release excipient, and in an amount about 0.5% to about 16% by weight of the final dosage form.

In the controlled release embodiments of the present invention, the sustained release excipient comprises from about 10 to about 99% by weight of a gelling agent comprising a heteropolysaccharide gum and a homopolysaccharide gum, from about 1 to about 20% by weight of a cationic crosslinking agent, and from about 0 to about 89% by weight of an inert pharmaceutical diluent. In other embodiments, the sustained release excipient comprises from about 10 to about 75% gelling agent, from about 2 to about 15% cationic crosslinking agent, and from about 30 to about 75% inert diluent. In yet other embodiments, the sustained release excipient comprises from about 30 to about 75% gelling agent, from about 5 to about 10% cationic cross-linking agent, and from about 15 to about 65% inert diluent.

The sustained release excipient used in this embodiment of the present invention (with or without the optional cationic cross-linking agent) may be further modified by incorporation of a hydrophobic material which slows the hydration of the gums without disrupting the hydrophilic matrix. This is accomplished in preferred embodiments of the present invention by granulating the sustained release excipient with the solution or dispersion of a hydrophobic material prior to the incorporation of the medicament. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The amount of hydrophobic material incorporated into the sustained release excipient is that which is effective to slow the hydration of the gums without disrupting the hydrophilic matrix formed upon exposure to an environmental fluid. In certain preferred embodiments of the present invention, the hydrophobic material is included in the sustained release excipient in an amount from about 1 to about 20% by weight. The solvent for the hydrophobic material may be an aqueous or organic solvent, or mixtures thereof.

Examples of commercially available alkylcelluloses are Aquacoat coating (aqueous dispersion of ethylcellulose available from FMC of Philadelphia, Pa.) and Surelease coating (aqueous dispersion of ethylcellulose available from Colorcon of West Point, Pa.). Examples of commercially available acrylic polymers suitable for use as the hydrophobic material include Eudragit RS and RL polymers (copolymers of acrylic and methacrylic acid esters having a low content (e.g., 1:20 or 1:40) of quaternary ammonium compounds available from Rohm America of Piscataway, N.J.).

The controlled release matrix useful in the present invention may also contain a cationic cross-linking agent such as calcium sulfate in an amount sufficient to cross-link the gelling agent and increase the gel strength, and an inert hydrophobic material such as ethyl cellulose in an amount sufficient to slow the hydration of the hydrophilic material without disrupting it. Preferably, the controlled release delivery system is prepared as a pre-manufactured granulation.

It has now been discovered that the bioavailability of controlled-release oxymorphone can be increased in patients with renal impairment (impaired kidney function), and is especially so in patients with moderately or severely impaired kidney function. Because of this, the oxymorphone levels in the blood of a patient with such renal impairment are higher than the levels that would be seen in a healthy patient receiving the same dose. As such, in order to avoid potential harmful effects, it is important to decrease the dose of controlled-release oxymorphone in patients with renal impairment.

Since it is important that a patient or physician is aware that the bioavailability is increased so as to avoid possible issues in dosing, one embodiment of the invention comprises informing the patient or the prescribing physician that the bioavailability of oxymorphone may be increased in some patients with renal impairment. Another embodiment of the invention comprises providing the patient or the patient's prescribing physician with prescribing information comprising instructions for dosing the controlled release oxymorphone composition to patients with renal impairment. For example, such instructions could be included in the labeling information, which can be the FDA-approved labeling, a package insert, or on the label itself. Other ways of communicating with patients or physicians are also available and are contemplated by the present invention. In another embodiment, the instructions provided comprise instructions to administer the lowest available dose.

EXAMPLES

Example 1

Two controlled release delivery systems are prepared by dry blending xanthan gum, locust bean gum, calcium sulfate dehydrate, and dextrose in a high speed mixed/granulator for 3 minutes. A slurry is prepared by mixing ethyl cellulose with alcohol. While running choppers/impellers, the slurry is added to the dry blended mixture, and granulated for another 3 minutes. The granulation is then dried to a LOD (loss on drying) of less than about 10% by weight. The granulation is then milled using 20 mesh screen. The relative quantities of the ingredients are listed in the table below.

TABLE 1

| | Controlled Release Delivery System | |
|---|---|---|
| Excipient | Formulation 1 (%) | Formulation 2 (%) |
| Locust Bean Gum, FCC | 25.0 | 30.0 |
| Xanthan Gum, NF | 25.0 | 30.0 |
| Dextrose, USP | 35.0 | 40.0 |
| Calcium Sulfate Dihydrate, NF | 10.0 | 0.0 |

TABLE 1-continued

Controlled Release Delivery System

| Excipient | Formulation 1 (%) | Formulation 2 (%) |
|---|---|---|
| Ethylcellulose, NF | 5.0 | 0.0 |
| Alcohol, SD3A (Anhydrous) | (10)[1] | (20.0)[1] |
| Total | 100.0 | 100.0 |

A series of tablets containing different amounts of oxymorphone hydrochloride were prepared using the controlled release delivery Formulation 1 shown in Table 1. The quantities of ingredients per tablet are as listed in the following table.

TABLE 2

Sample Tablets of Differing Strengths

| Component | Amount in Tablet (mg) | | | | |
|---|---|---|---|---|---|
| Oxymorphone HCl, USP (mg) | 5 | 10 | 20 | 40 | 80 |
| Controlled release delivery system | 160 | 160 | 160 | 160 | 160 |
| Silicified microcrystalline cellulose, N.F. | 20 | 20 | 20 | 20 | 20 |
| Sodium stearyl fumarate, NF | 2 | 2 | 2 | 2 | 2 |
| Total weight | 187 | 192 | 202 | 222 | 262 |
| Opadry (colored) | 7.48 | 7.68 | 8.08 | 8.88 | 10.48 |
| Opadry (clear) | 0.94 | 0.96 | 1.01 | 1.11 | 1.31 |

Examples 2, 3 and 4

Two batches of 20 mg tablets were prepared as described above, using the controlled release delivery system of Formulation 1. One batch was formulated to provide relatively fast controlled release, the other batch was formulated to provide relatively slow controlled release. Compositions of the tablets are shown in the following table.

TABLE 3

Slow and Fast Release Compositions

| Ingredients | Example 2 Slow (mg) | Example 3 Fast (mg) | Example 4 Fast (mg) |
|---|---|---|---|
| Oxymorphone HCl, USP | 20 | 20 | 20 |
| Controlled Release Delivery System | 360 | 160 | 160 |
| Silicified Microcrystalline Cellulose, NF | 20 | 20 | 20 |
| Sodium stearyl fumarate, NF | 4 | 2 | 2 |
| Total weight | 404 | 202 | 202 |
| Coating (color or clear) | 12 | 12 | 9 |

The tablets of Examples 2, 3, and 4 were tested for in vitro release rate according to USP Procedure Drug Release USP No. 23. Release rate is a critical variable in attempting to control the blood plasma levels of oxymorphone and 6-hydroxyoxymorphone in a patient. Results are shown in the following Table 4.

TABLE 4

Release Rates of Slow and Fast Release Tablets

| Time (hr) | Example 2 (Slow Release) | Example 3 (Fast Release) | Example 4 (Fast Release) |
|---|---|---|---|
| 0.5 | 18.8 | 21.3 | 20.1 |
| 1 | 27.8 | 32.3 | 31.7 |
| 2 | 40.5 | 47.4 | 46.9 |
| 3 | 50.2 | 58.5 | 57.9 |
| 4 | 58.1 | 66.9 | 66.3 |
| 5 | 64.7 | 73.5 | 74.0 |
| 6 | 70.2 | 78.6 | 83.1 |
| 8 | 79.0 | 86.0 | 92.0 |
| 10 | 85.3 | 90.6 | 95.8 |
| 12 | 89.8 | 93.4 | 97.3 |

Clinical Studies

Three clinical studies were conducted to assess the bioavailability (rate and extent of absorption) of oxymorphone. Study 1 addressed the relative rates of absorption of controlled release (CR) oxymorphone tablets (of Examples 2 and 3) and oral oxymorphone solution in fasted patients. Study 2 addressed the relative rates of absorption of CR oxymorphone tablets (of Examples 2 and 3) and oral oxymorphone solution in fed patients. Study 3 addressed the relative rates of absorption of CR oxymorphone tablets (of Example 4) and oral oxymorphone solution in fed and fasted patients.

The blood plasma levels set forth herein as appropriate to achieve the objects of the present invention are mean blood plasma levels. As an example, if the blood plasma level of oxymorphone in a patient 12 hours after administration of a tablet is said to be at least 0.5 ng/ml, any particular individual may have lower blood plasma levels after 12 hours. However, the mean minimum concentration should meet the limitation set forth. To determine mean parameters, a study should be performed with a minimum of 8 adult subjects, in a manner acceptable for filing an application for drug approval with the US Food and Drug Administration. In cases where large fluctuations are found among patients, further testing may be necessary to accurately determine mean values.

For all studies, the following procedures were followed, unless otherwise specified for a particular study.

The subjects were not to consume any alcohol-, caffeine-, or xanthine-containing foods or beverages for 24 hours prior to receiving study medication for each study period. Subjects were to be nicotine and tobacco free for at least 6 months prior to enrolling in the study. In addition, over-the-counter medications were prohibited 7 days prior to dosing and during the study. Prescription medications were not allowed 14 days prior to dosing and during the study.

Pharmacokinetic and Statistical Methods

The following pharmacokinetic parameters were computed from the plasma oxymorphone concentration-time data:

$AUC_{(0-t)}$ Area under the drug concentration-time curve from time zero to the time of the last quantifiable concentration (Ct), calculated using linear trapezoidal summation.

$AUC_{(0-inf)}$ Area under the drug concentration-time curve from time zero to infinity. $AUC_{(0-inf)} = AUC_{(0-t)} + Ct/K_{el}$, where $K_{el}$ is the terminal elimination rate constant.

$AUC_{(0-24)}$ Partial area under the drug concentration-time curve from time zero to 24 hours.

$C_{max}$ Maximum observed drug concentration.

$T_{max}$ Time of the observed maximum drug concentration.

$K_{el}$ Elimination rate constant based on the linear regression of the terminal linear portion of the LN (concentration) time curve.

Terminal elimination rate constants for use in the above calculations were in turn computed using linear regression of a minimum of three time points, at least two of which were consecutive. $K_{el}$ values for which correlation coefficients were less than or equal to 0.8 were not reported in the pharmacokinetic parameter tables or included in the statistical analysis. Thus $AUC_{(0-inf)}$ was also not reported in these cases.

A parametric (normal-theory) general linear model was applied to each of the above parameters (excluding $T_{max}$), and the LN-transformed parameters $C_{max}$, $AUC_{(0-24)}$, $AUC_{(0-t)}$, and $AUC_{(0-inf)}$. Initially, the analysis of variance (ANOVA) model included the following factors: treatment, sequence, subject within sequence, period, and carryover effect. If carryover effect was not significant, it was dropped from the model. The sequence effect was tested using the subject within sequence mean square, and all other main effects were tested using the residual error (error mean square).

Plasma oxymorphone concentrations were listed by subject at each collection time and summarized using descriptive statistics. Pharmacokinetic parameters were also listed by subject and summarized using descriptive statistics.

Study 1—Two Controlled Release Formulations; Fasted Patients

Healthy volunteers received a single oral dose of 20 mg CR oxymorphone taken with 240 ml water after a 10-hour fast. Subjects received the tablets of Example 2 (Treatment 1A) or Example 3 (Treatment 1B). Further subjects were given a single oral dose of 10 mg/10 ml oxymorphone solution in 180 ml apple juice followed with 60 ml water (Treatment 1C). The orally dosed solution was used to simulate an immediate release (IR) dose.

This study had a single-center, open-label, randomized, three-way crossover design using fifteen subjects. Subjects were in a fasted state following a 10-hour overnight fast. There was a 14-day washout interval between the three dose administrations. The subjects were confined to the clinic during each study period. Subjects receiving Treatment 1C were confined for 18 hours and subjects receiving Treatments 1A or 1B were confined for 48 hours after dosing. Ten-milliliter blood samples were collected during each study period at the 0 hour (predose), and at 0.5, 1, 1.5, 2, 3, 4, 5, 6, 7, 8, 10, 12, 14, 16, 18, 20, 24, 28, 32, 36, and 48 hours postdose for subjects receiving Treatment 1A or 1B and 0, 0.25, 0.5, 0.75, 1, 1.25, 1.5, 1.75, 2, 2.5, 3, 4, 5, 6, 7, 8, 10, 12, 14, 16, and 18 hours post-dose. The mean plasma concentration of oxymorphone versus time for each treatment across all subjects is shown in table 5.

TABLE 5

| Mean Plasma Concentration vs. Time (ng/ml) | | | |
| --- | --- | --- | --- |
| Time (hr) | Treatment 1A | Treatment 1B | Treatment 1C |
| 0 | 0.000 | 0.000 | 0.0000 |
| 0.25 | | | 0.9489 |
| 0.5 | 0.2941 | 0.4104 | 1.3016 |
| 0.75 | | | 1.3264 |
| 1 | 0.5016 | 0.7334 | 1.3046 |
| 1.25 | | | 1.2041 |
| 1.5 | 0.5951 | 0.8192 | 1.0813 |
| 1.75 | | | 0.9502 |
| 2 | 0.6328 | 0.7689 | 0.9055 |
| 2.5 | | | 0.7161 |
| 3 | 0.5743 | 0.7341 | 0.6689 |
| 4 | 0.5709 | 0.6647 | 0.4879 |
| 5 | 0.7656 | 0.9089 | 0.4184 |
| 6 | 0.7149 | 0.7782 | 0.3658 |
| 7 | 0.6334 | 0.6748 | 0.3464 |
| 8 | 0.5716 | 0.5890 | 0.2610 |
| 10 | 0.4834 | 0.5144 | 0.2028 |
| 12 | 0.7333 | 0.6801 | 0.2936 |
| 14 | 0.6271 | 0.6089 | 0.2083 |
| 16 | 0.4986 | 0.4567 | 0.1661 |
| 18 | 0.4008 | 0.3674 | 0.1368 |
| 20 | 0.3405 | 0.2970 | |
| 24 | 0.2736 | 0.2270 | |
| 28 | 0.3209 | 0.2805 | |
| 32 | 0.2846 | 0.2272 | |
| 36 | 0.2583 | 0.1903 | |
| 48 | 0.0975 | 0.0792 | |

Figure 5:
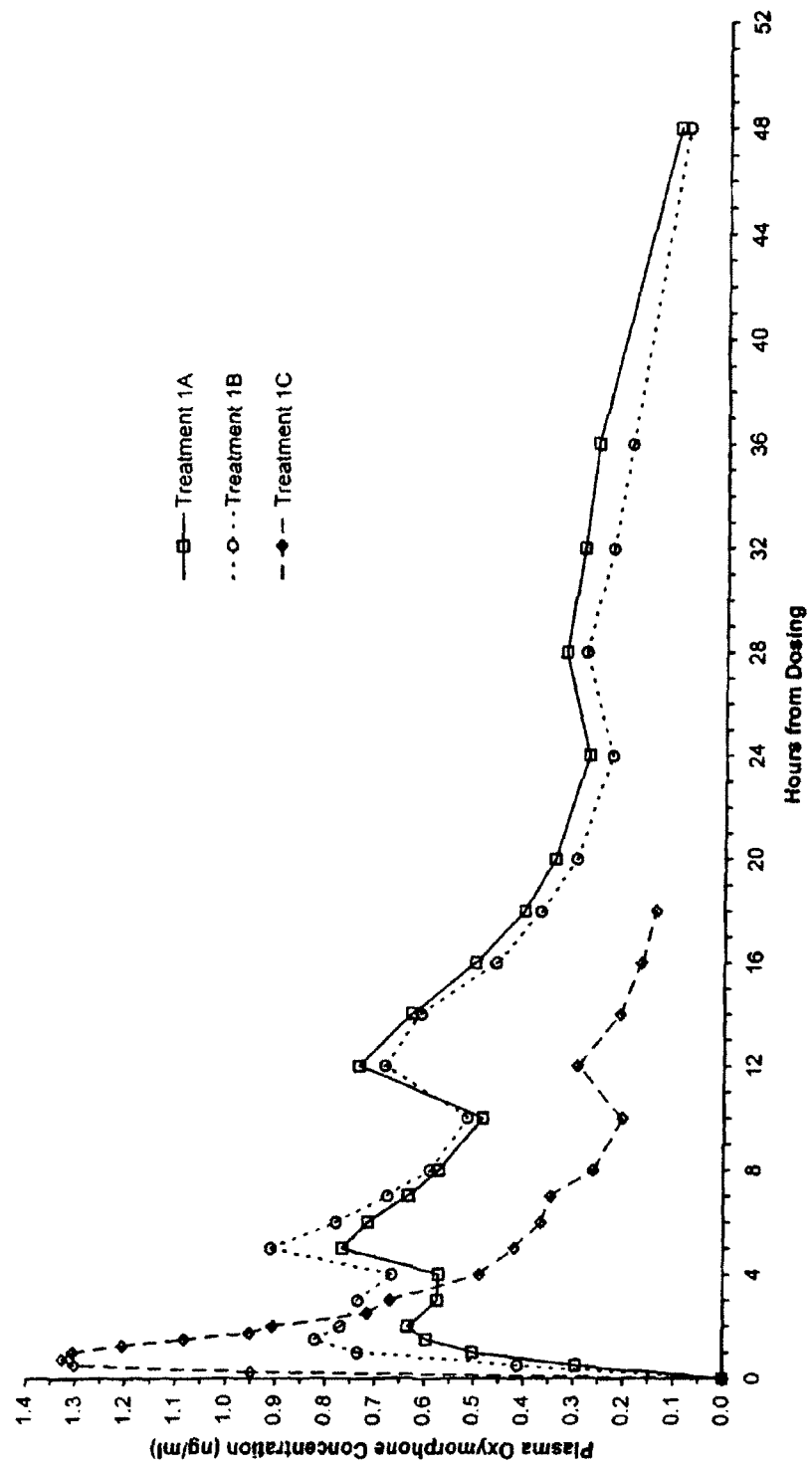
FIG. 5 is a graph of the mean blood plasma concentration of oxymorphone versus time for clinical study 1.

The results are shown graphically in FIG. 5. In both Table 5 and FIG. 5, the results are normalized to a 20 mg dosage. The immediate release liquid of Treatment 1C shows a classical curve, with a high and relatively narrow peak, followed by an exponential drop in plasma concentration. However, the controlled release oxymorphone tablets exhibit triple peaks in blood plasma concentration. The first peak occurs (on average) at around 3 hours. The second peak of the mean blood plasma concentration is higher than the first, occurring around 6-7 hours, on average).

Occasionally, in an individual, the first peak is higher than the second, although generally this is not the case. This makes it difficult to determine the time to maximum blood plasma concentration ($T_{max}$) because if the first peak is higher than the second, maximum blood plasma concentration ($C_{max}$) occurs much earlier (at around 3 hours) than in the usual case where the second peak is highest. Therefore, when we refer to the time to peak plasma concentration ($T_{max}$) unless otherwise specified, we refer to the time to the second peak. Further, when reference is made to the second peak, we refer to the time or blood plasma concentration at the point where the blood plasma concentration begins to drop the second time. Generally, where the first peak is higher than the second, the difference in the maximum blood plasma concentration at the two peaks is small. Therefore, this difference (if any) was ignored and the reported $C_{max}$ was the true maximum blood plasma concentration and not the concentration at the second peak.

TABLE 6

| Pharmacokinetic Parameters of Plasma Oxymorphone for Study 1 | | | | | | |
| --- | --- | --- | --- | --- | --- | --- |
| | Treatment 1A | | Treatment 1B | | Treatment 1C | |
| | Mean | SD | Mean | SD | Mean | SD |
| $C_{max}$ | 0.8956 | 0.2983 | 1.0362 | 0.3080 | 2.9622 | 1.0999 |
| $T_{max}$ | 7.03 | 4.10 | 4.89 | 3.44 | 0.928 | 0.398 |
| $AUC_{(0-t)}$ | 17.87 | 6.140 | 17.16 | 6.395 | 14.24 | 5.003 |
| $AUC_{(0-inf)}$ | 19.87 | 6.382 | 18.96 | 6.908 | 16.99 | 5.830 |
| $T_{1/2el}$ | 10.9 | 2.68 | 11.4 | 2.88 | 6.96 | 4.61 |

Units: $C_{max}$ in ng/ml, $T_{max}$ in hours, AUC in ng*hr/ml, $T_{1/2el}$ in hours.

Relative bioavailability determinations are set forth in Tables 7 and 8. For these calculations, AUC was normalized for all treatments to a 20 mg dose.

TABLE 7

Relative Bioavailability ($F_{rel}$) Determination Based on $AUC_{(0-inf)}$

| $F_{rel}$ (1A vs. 1C) | $F_{rel}$ (1B vs. 1C) | $F_{rel}$ (1A vs. 1B) |
|---|---|---|
| 1.193 ± 0.203 | 1.121 ± 0.211 | 1.108 ± 0.152 |

TABLE 8

Relative Bioavailability Determination Based on $AUC_{(0-18)}$

| $F_{rel}$ (1A vs. 1C) | $F_{rel}$ (1B vs. 1C) | $F_{rel}$ (1A vs. 1B) |
|---|---|---|
| 0.733 ± 0.098 | 0.783 ± 0.117 | 0.944 ± 0.110 |

Study 2—Two CR Formulations; Fed Patients

Healthy volunteers received a single oral dose of 20 mg CR oxymorphone taken with 240 ml water in a fed state. Subjects received the tablets of Example 2 (Treatment 2A) or Example 3 (Treatment 2B). Further subjects were given a single oral dose of 10 mg/10 ml oxymorphone solution in 180 ml apple juice followed with 60 ml water (Treatment 2C). The orally dosed solution was used to simulate an immediate release (IR) dose.

This study had a single-center, open-label, randomized, three-way crossover design using fifteen subjects. The subjects were in a fed state, after a 10-hour overnight fast followed by a standardized FDA high-fat breakfast. There was a 14-day washout interval between the three dose administrations. The subjects were confined to the clinic during each study period. Subjects receiving Treatment 2C were confined for 18 hours and subjects receiving Treatments 2A or 2B were confined for 48 hours after dosing. Ten-milliliter blood samples were collected during each study period at the 0 hour (predose), and at 0.5, 1, 1.5, 2, 3, 4, 5, 6, 7, 8, 10, 12, 14, 16, 18, 20, 24, 28, 32, 36, and 48 hours postdose for subjects receiving Treatment 2A or 2B and 0, 0.25, 0.5, 0.75, 1, 1.25, 1.5, 1.75, 2, 2.5, 3, 4, 5, 6, 7, 8, 10, 12, 14, 16, and 18 hours postdose. The mean plasma concentration of oxymorphone versus time for each treatment across all subjects is shown in table 9.

TABLE 9

Mean Plasma Concentration vs. Time (ng/ml)

| Time (hr) | Treatment 2A | Treatment 2B | Treatment 2C |
|---|---|---|---|
| 0 | 0.000 | 0.000 | 0.0000 |
| 0.25 | | | 1.263 |
| 0.5 | 0.396 | .0553 | 1.556 |
| 0.75 | | | 1.972 |
| 1 | 0.800 | 1.063 | 1.796 |
| 1.25 | | | 1.795 |
| 1.5 | 1.038 | 1.319 | 1.637 |
| 1.75 | | | 1.467 |
| 2 | 1.269 | 1.414 | 1.454 |
| 2.5 | | | 1.331 |
| 3 | 1.328 | 1.540 | 1.320 |
| 4 | 1.132 | 1.378 | 1.011 |
| 5 | 1.291 | 1.609 | 0.731 |
| 6 | 1.033 | 1.242 | 0.518 |
| 7 | 0.941 | 0.955 | 0.442 |
| 8 | 0.936 | 0.817 | 0.372 |
| 10 | 0.669 | 0.555 | 0.323 |
| 12 | 0.766 | 0.592 | 0.398 |
| 14 | 0.641 | 0.519 | 0.284 |
| 16 | 0.547 | 0.407 | 0.223 |
| 18 | 0.453 | 0.320 | 0.173 |
| 20 | 0.382 | 0.280 | |
| 24 | 0.315 | 0.254 | |
| 28 | 0.352 | 0.319 | |
| 32 | 0.304 | 0.237 | |
| 36 | 0.252 | 0.207 | |
| 48 | 0.104 | 0.077 | |

Figure 6:
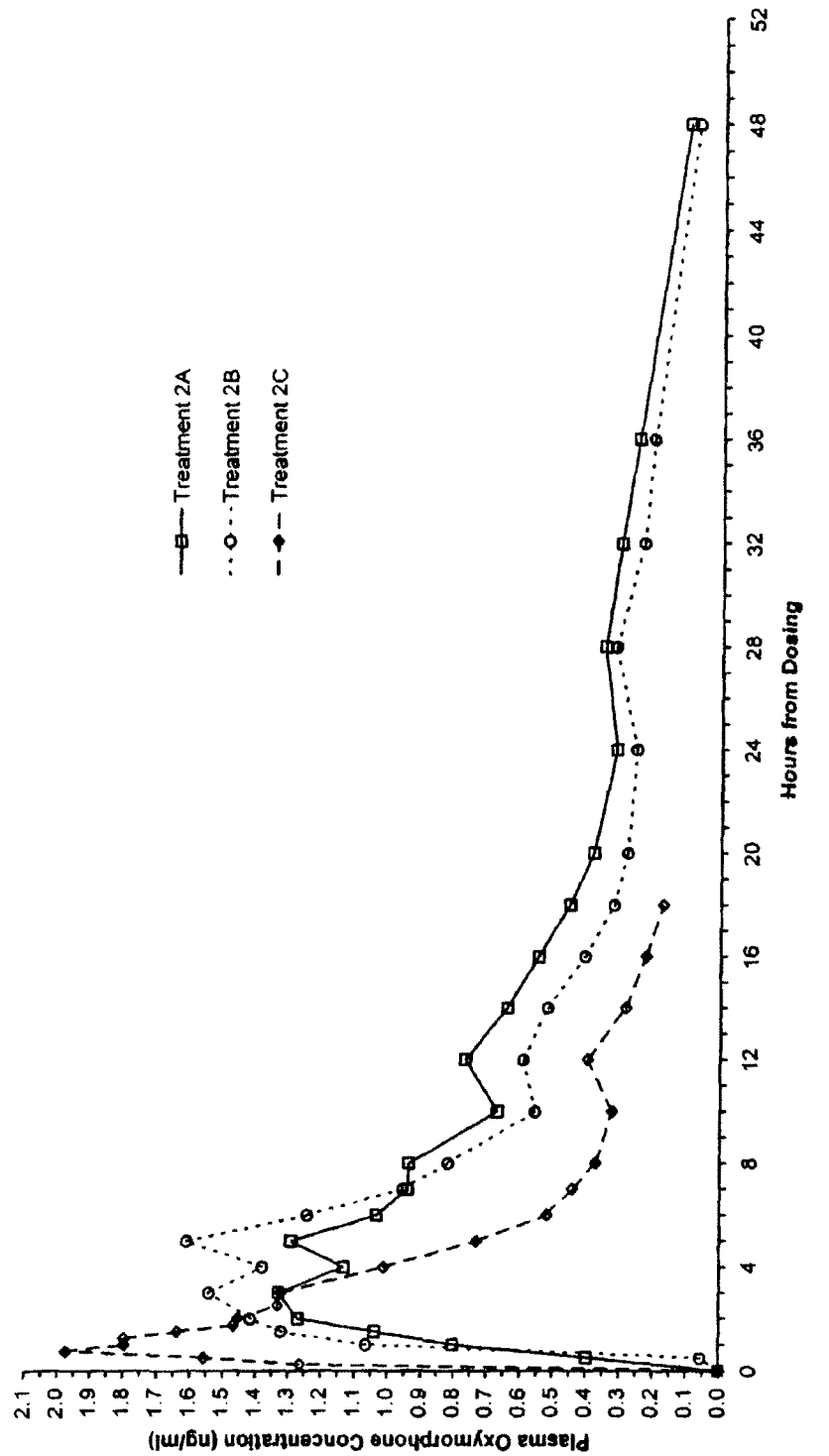
FIG. 6 is a graph of the mean blood plasma concentration of oxymorphone versus time for clinical study 2.

The results are shown graphically in FIG. 6. Again, the results have been normalized to a 20 mg dosage. As with Study 1, the immediate release liquid of Treatment 2C shows a classical curve, with a high and relatively narrow peak, followed by an exponential drop in plasma concentration, while the controlled release oxymorphone tablets exhibit triple peaks in blood plasma concentration. Thus, again when we refer to the time to peak plasma concentration ($T_{max}$) unless otherwise specified, we refer to the time to the second peak.

TABLE 10

Pharmacokinetic Parameters of Plasma Oxymorphone for Study 2

| | Treatment 2A | | Treatment 2B | | Treatment 2C | |
|---|---|---|---|---|---|---|
| | Mean | SD | Mean | SD | Mean | SD |
| $C_{max}$ | 1.644 | 0.365 | 1.944 | 0.465 | 4.134 | 0.897 |
| $T_{max}$ | 3.07 | 1.58 | 2.93 | 1.64 | 0.947 | 0.313 |
| $AUC_{(0-t)}$ | 22.89 | 5.486 | 21.34 | 5.528 | 21.93 | 5.044 |
| $AUC_{(0-inf)}$ | 25.28 | 5.736 | 23.62 | 5.202 | 24.73 | 6.616 |
| $T_{1/2el}$ | 12.8 | 3.87 | 11.0 | 3.51 | 5.01 | 2.02 |

Units: $C_{max}$ in ng/ml, $T_{max}$ in hours, AUC in ng*hr/ml, $T_{1/2el}$ in hours.

In Table 10, the $T_{max}$ has a large standard deviation due to the two comparable peaks in blood plasma concentration. Relative bioavailability determinations are set forth in Tables 11 and 12.

TABLE 11

Relative Bioavailability Determination Based on $AUC_{(0-inf)}$

| $F_{rel}$ (2A vs. 2C) | $F_{rel}$ (2B vs. 2C) | $F_{rel}$ (2A vs. 2B) |
|---|---|---|
| 1.052 ± 0.187 | 0.949 ± 0.154 | 1.148 ± 0.250 |

TABLE 12

Relative bioavailability Determination Based on $AUC_{(0-48)}$

| $F_{rel}$ (2A vs. 2C) | $F_{rel}$ (2B vs. 2C) | $F_{rel}$ (2A vs. 2B) |
|---|---|---|
| 0.690 ± 0.105 | 0.694 ± 0.124 | 1.012 ± 0.175 |

As may be seen from tables 5 and 10 and FIGS. 1 and 2, the $C_{max}$ for the CR tablets (treatments 1A, 1B, 2A and 2B) is considerably lower, and the $T_{max}$ much higher than for the immediate release oxymorphone. The blood plasma level of oxymorphone remains high well past the 8 (or even the 12) hour dosing interval desired for an effective controlled release tablet.

Study 3—One Controlled Release Formulation; Fed and Fasted Patients

This study had a single-center, open-label, analytically blinded, randomized, four-way crossover design. Subjects randomized to Treatment 3A and Treatment 3C, as described below, were in a fasted state following a 10-hour overnight fast. Subjects randomized to Treatment 3B and Treatment 3D, as described below, were in the fed state, having had a high fat meal, completed ten minutes prior to dosing. There was a 14-day washout interval between the four dose administrations. The subjects were confined to the clinic during each study period. Subjects assigned to receive Treatment 3A and Treatment 3B were discharged from the clinic on Day 3 following the 48-hour procedures, and subjects assigned to receive Treatment 3C and Treatment 3D were discharged from the clinic on Day 2 following the 36-hour procedures. On Day 1 of each study period the subjects received one of four treatments:

Treatments 3A and 3B: Oxymorphone controlled release 20 mg tablets from Example 3. Subjects randomized to Treatment 3A received a single oral dose of one 20 mg oxymorphone controlled release tablet taken with 240 ml of water after a 10-hour fasting period. Subjects randomized to Treatment 3B received a single oral dose of one 20 mg oxymorphone controlled release tablet taken with 240 ml of water 10 minutes after a standardized high fat meal.

Treatments 3C and 3D: oxymorphone HCl solution, USP, 1.5 mg/ml 10 ml vials. Subjects randomized to Treatment 3C received a single oral dose of 10 mg (6.7 ml) oxymorphone solution taken with 240 ml of water after a 10-hour fasting period. Subjects randomized to Treatment 3D received a single oral dose of 10 mg (6.7 ml) oxymorphone solution taken with 240 ml of water 10 minutes after a standardized high-fat meal.

A total of 28 male subjects were enrolled in the study, and 24 subjects completed the study. The mean age of the subjects was 27 years (range of 19 through 38 years), the mean height of the subjects was 69.6 inches (range of 64.0 through 75.0 inches), and the mean weight of the subjects was 169.0 pounds (range 117.0 through 202.0 pounds).

A total of 28 subjects received at least one treatment. Only subjects who completed all 4 treatments were included in the summary statistics and statistical analysis.

Blood samples (7 ml) were collected during each study period at the 0 hour (predose), and at 0.5, 1, 1.5, 2, 3, 4, 5, 6, 8, 10, 12, 14, 16, 20, 24, 30, 36, and 48 hours post-dose (19 samples) for subjects randomized to Treatment 3A and Treatment 3B. Blood samples (7 ml) were collected during each study period at the 0 hour (predose), and at 0.25, 0.5, 0.75, 1, 1.25, 1.5, 1.75, 2, 3, 4, 5, 6, 8, 10, 12, 14, 16, 20, and 36 hours post-dose (21 samples) for subjects randomized to Treatment 3C and Treatment 3D.

Figure 7:
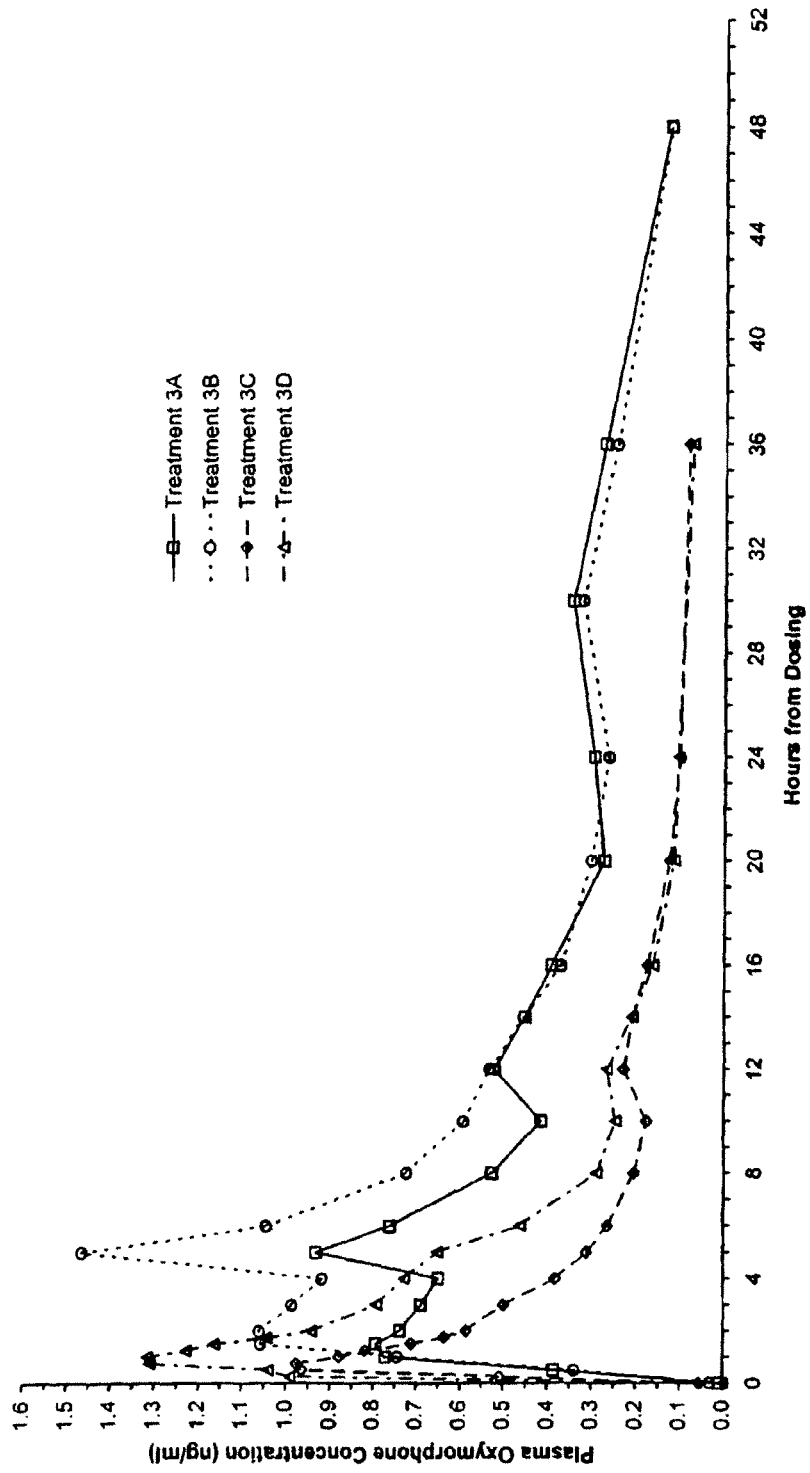
FIG. 7 is a graph of the mean blood plasma concentration of oxymorphone versus time for clinical study 3.

The mean oxymorphone plasma concentration versus time curves for Treatments 3A, 3B, 3C, and 3D are presented in FIG. 7. The results have been normalized to a 20 mg dosage. The data is contained in Table 13. The arithmetic means of the plasma oxymorphone pharmacokinetic parameters and the statistics for all Treatments are summarized in Table 14.

TABLE 13

Mean Plasma Concentration vs. Time (ng/ml)

| Time (hr) | Treatment 3A | Treatment 3B | Treatment 3C | Treatment 3D |
|---|---|---|---|---|
| 0 | 0.0084 | 0.0309 | 0.0558 | 0.0000 |
| 0.25 | | | 0.5074 | 0.9905 |
| 0.5 | 0.3853 | 0.3380 | 0.9634 | 1.0392 |
| 0.75 | | | 0.9753 | 1.3089 |
| 1 | 0.7710 | 0.7428 | 0.8777 | 1.3150 |
| 1.25 | | | 0.8171 | 1.2274 |
| 1.5 | 0.7931 | 1.0558 | 0.7109 | 1.1638 |
| 1.75 | | | 0.6357 | 1.0428 |
| 2 | 0.7370 | 1.0591 | 0.5851 | 0.9424 |
| 3 | 0.6879 | 0.9858 | 0.4991 | 0.7924 |
| 4 | 0.6491 | 0.9171 | 0.3830 | 0.7277 |
| 5 | 0.9312 | 1.4633 | 0.3111 | 0.6512 |
| 6 | 0.7613 | 1.0441 | 0.2650 | 0.4625 |
| 8 | 0.5259 | 0.7228 | 0.2038 | 0.2895 |
| 10 | 0.4161 | 0.5934 | 0.1768 | 0.2470 |
| 12 | 0.5212 | 0.5320 | 0.2275 | 0.2660 |
| 14 | 0.4527 | 0.4562 | 0.2081 | 0.2093 |
| 16 | 0.3924 | 0.3712 | 0.1747 | 0.1623 |
| 20 | 0.2736 | 0.3021 | 0.1246 | 0.1144 |
| 24 | 0.2966 | 0.2636 | 0.1022 | 0.1065 |
| 30 | 0.3460 | 0.3231 | | |
| 36 | 0.2728 | 0.2456 | 0.0841 | 0.0743 |
| 48 | 0.1263 | 0.1241 | | |

TABLE 14

Pharmacokinetic Parameters of Plasma Oxymorphone for Study 3

| | Treatment 3B | | Treatment 3A | | Treatment 3C | | Treatment 3D | |
|---|---|---|---|---|---|---|---|---|
| | Mean | SD | Mean | SD | Mean | SD | Mean | SD |
| $C_{max}$ | 1.7895 | 0.6531 | 1.1410 | 0.4537 | 2.2635 | 1.0008 | 3.2733 | 1.3169 |
| $T_{max}$ | 5.65 | 9.39 | 5.57 | 7.14 | 0.978 | 1.14 | 1.11 | 7.768 |
| $AUC_{(0-24)}$ | 14.27 | 4.976 | 11.64 | 3.869 | 12.39 | 4.116 | 17.30 | 5.259 |

TABLE 14-continued

Pharmacokinetic Parameters of Plasma Oxymorphone for Study 3

| | Treatment 3B | | Treatment 3A | | Treatment 3C | | Treatment 3D | |
|---|---|---|---|---|---|---|---|---|
| | Mean | SD | Mean | SD | Mean | SD | Mean | SD |
| $AUC_{(0-t)}$ | 19.89 | 6.408 | 17.71 | 8.471 | 14.53 | 4.909 | 19.20 | 6.030 |
| $AUC_{(0-inf)}$ | 21.29 | 6.559 | 19.29 | 5.028 | 18.70 | 6.618 | 25.86 | 10.03 |
| $T_{1/2el}$ | 12.0 | 3.64 | 12.3 | 3.99 | 16.2 | 11.4 | 20.6 | 19.3 |

The relative bioavailability calculations are summarized in tables 15 and 16.

TABLE 15

Relative Bioavailability Determination Based on $AUC_{(0-inf)}$

| $F_{rel}$ (3A vs. 3C) | $F_{rel}$ (3B vs. 3D) | $F_{rel}$ (3D vs. 3C) | $F_{rel}$ (3B vs. 3A) |
|---|---|---|---|
| 1.040 ± 0.1874 | 0.8863 ± 0.2569 | 1.368 ± 0.4328 | 1.169 ± 0.2041 |

TABLE 16

Relative bioavailability Determination Based on $AUC_{(0-24)}$

| $F_{rel}$ (3A vs. 2C) | $F_{rel}$ (3B vs. 3D) | $F_{rel}$ (3D vs. 3C) | $F_{rel}$ (3B vs. 3A) |
|---|---|---|---|
| 0.9598 ± 0.2151 | 0.8344 ± 0.100 | 1.470 ± 0.3922 | 1.299 ± 0.4638 |

The objectives of this study were to assess the relative bioavailability of oxymorphone from oxymorphone controlled release (20 mg) compared to oxymorphone oral solution (10 mg) under both fasted and fed conditions, and to determine the effect of food on the bioavailability of oxymorphone from the controlled release formulation, oxymorphone CR, and from the oral solution.

The presence of a high fat meal had a substantial effect on the oxymorphone $C_{max}$, but less of an effect on oxymorphone AUC from oxymorphone controlled release tablets. Least Squares (LS) mean $C_{max}$ was 58% higher and LS mean $AUC_{(0-t)}$ and $AUC_{(0-inf)}$ were 18% higher for the fed condition (Treatment B) compared to the fasted condition (Treatment A) based on LN-transformed data. This was consistent with the relative bioavailability determination from $AUC_{(0-inf)}$ since mean $F_{rel}$ was 1.17. Mean $T_{max}$ values were similar (approximately 5.6 hours), and no significant difference in $T_{max}$ was shown using nonparametric analysis. Half value durations were significantly different between the two treatments.

The effect of food on oxymorphone bioavailability from the oral solution was more pronounced, particularly in terms of AUC. LS mean $C_{max}$ was 50% higher and LS mean $AUC_{(0-t)}$ and $AUC_{(0-inf)}$ were 32-34% higher for the fed condition (Treatment D) compared to the fasted condition (Treatment C) based on LN-transformed data. This was consistent with the relative bioavailability determination from $AUC_{(0-inf)}$ since mean $F_{rel}$ was 1.37. Mean $T_{max}$ (approximately 1 hour) was similar for the two treatments and no significant difference was shown.

Under fasted conditions, oxymorphone controlled release 20 mg tablets exhibited similar extent of oxymorphone availability compared to 10 mg oxymorphone oral solution normalized to a 20 mg dose (Treatment A versus Treatment C). From LN-transformed data, LS mean $AUC_{(0-t)}$ was 17% higher for oxymorphone CR, whereas LS mean $AUC_{(0-inf)}$ values were nearly equal (mean ratio=99%). Mean $F_{rel}$ values calculated from $AUC_{(0-inf)}$ and $AUC_{(0-24)}$, (1.0 and 0.96, respectively) also showed similar extent of oxymorphone availability between the two treatments.

As expected, there were differences in parameters reflecting rate of absorption. LS mean $C_{max}$ was 49% lower for oxymorphone controlled release tablets compared to the dose-normalized oral solution, based on LN-transformed data. Half-value duration was significantly longer for the controlled release formulation (means, 12 hours versus 2.5 hours).

Under fed conditions, oxymorphone availability from oxymorphone controlled release 20 mg was similar compared to 10 mg oxymorphone oral solution normalized to a 20 mg dose (Treatment B versus Treatment D). From LN-transformed data, LS mean $AUC_{(0-inf)}$ was 12% lower for oxymorphone CR. Mean $F_{rel}$ values calculated from $AUC_{(0-inf)}$ and $AUC_{(0-24)}$, (0.89 and 0.83 respectively) also showed similar extent of oxymorphone availability from the tablet. As expected, there were differences in parameters reflecting rate of absorption. LS mean $C_{max}$ was 46% lower for oxymorphone controlled release tablets compared to the dose-normalized oral solution, based on LN-transformed data. Mean $T_{max}$ was 5.7 hours for the tablet compared to 1.1 hours for the oral solution. Half-value duration was significantly longer for the controlled release formulation (means, 7.8 hours versus 3.1 hours).

The presence of a high fat meal did not appear to substantially affect the availability of 6-hydroxyoxymorphone following administration of oxymorphone controlled release tablets. LS mean ratios were 97% for $AUC_{(0-t)}$ and 91% for $C_{max}$ (Treatment B versus A), based on LN-transformed data. This was consistent with the relative bioavailability determination from $AUC_{(0-24)}$, since mean $F_{rel}$ was 0.97. Mean $T_{max}$ was later for the fed treatment compared to the fasted treatment (5.2 and 3.6 hours, respectively), and difference was significant.

Under fasted conditions, oxymorphone controlled release 20 mg tablets exhibited similar availability of 6-hydroxyoxymorphone compared to 10 mg oxymorphone oral solution normalized to a 20 mg dose (Treatment A versus Treatment C). From LN-transformed data, LS mean ratio for $AUC_{(0-t)}$ was 104.5%. Mean $F_{rel}$ (0.83) calculated from $AUC_{(0-24)}$ also showed similar extent of oxymorphone availability between the two treatments. Mean $T_{max}$ was 3.6 hours for the tablet compared to 0.88 for the oral solution. Half-value duration was significantly longer for the controlled release formulation (means, 11 hours versus 2.2 hours).

Under fed conditions, availability of 6-hydroxyoxymorphone from oxymorphone controlled release 20 mg was similar compared to 10 mg oxymorphone oral solution normalized to a 20 mg dose (Treatment B versus Treatment D). From LN-transformed data, LS mean $AUC_{(0-t)}$ was 14% higher for oxymorphone CR. Mean $F_{rel}$ (0.87) calculated from $AUC_{(0-24)}$ also indicated similar extent of availability between the treatments. Mean $T_{max}$ was 5.2 hours for the tablet compared to 1.3 hour for the oral solution. Half-value duration was significantly longer for the controlled release formulation (means, 14 hours versus 3.9 hours).

The extent of oxymorphone availability from oxymorphone controlled release 20 mg tablets was similar under fed and fasted conditions since there was less than a 20% difference in LS mean $AUC_{(0-t)}$ and $AUC_{(0-inf)}$ values for each treatment, based on LN-transformed data. $T_{max}$ was unaffected by food; however, LS mean $C_{max}$ was increased 58% in the presence of the high fat meal. Both rate and extent of oxymorphone absorption from the oxymorphone oral solution were affected by food since LS mean $C_{max}$ and AUC values were increased approximately 50 and 30%, respectively. $T_{max}$ was unaffected by food. Under both fed and fasted conditions, oxymorphone controlled release tablets exhibited similar extent of oxymorphone availability compared to oxymorphone oral solution since there was less than a 20% difference in LS mean AUC(0-t) and AUC(0-inf) values for each treatment.

Bioavailability of 6-hydroxyoxymorphone following oxymorphone controlled release 20 mg tablets was also similar under fed and fasted conditions since there was less than a 20% difference in LS mean $C_{max}$ and AUC values for each treatment. $T_{max}$ was later for the fed condition. The presence of food did not affect the extent of availability from oxymorphone oral solution since LS mean AUC values were less than 20% different. However, $C_{max}$ was decreased 35% in the presence of food. $T_{max}$ was unaffected by food. Under both fed and fasted conditions, oxymorphone controlled release tablets exhibited similar extent of availability compared to oxymorphone oral solution since there was less than a 20% difference in LS mean AUC values for each treatment.

Figure 8:
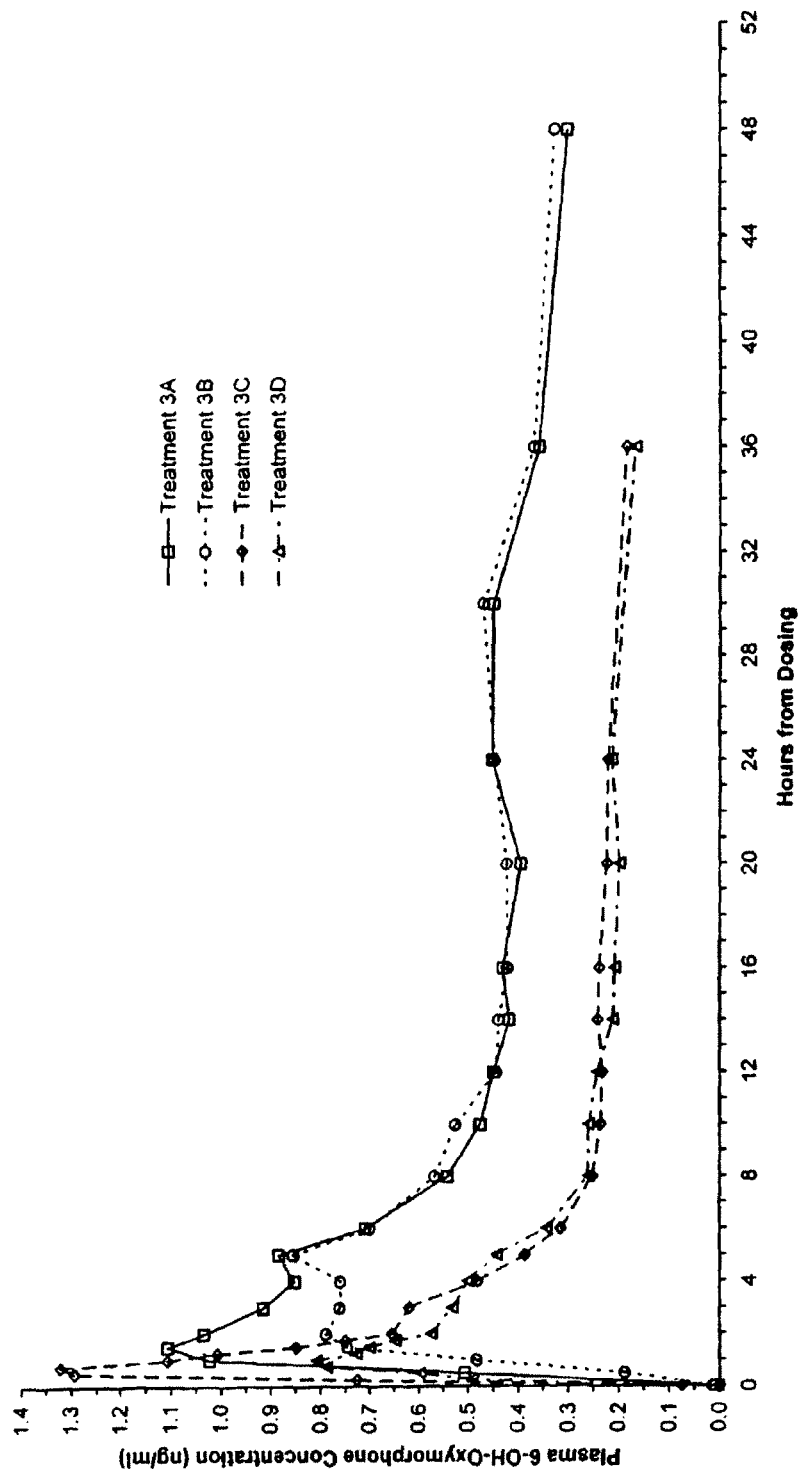
FIG. 8 is a graph of the mean blood plasma concentration of 6-hydroxy oxymorphone versus time for clinical study 3.

The mean 6-OH oxymorphone plasma concentration versus time curves for Treatments 3A, 3B, 3C, and 3D are presented in FIG. 8. The data is contained in Table 17.

TABLE 17

Mean Plasma Concentration vs. Time (ng/ml)
6-Hydroxyoxymorphone

| Time (hr) | Treatment 3A | Treatment 3B | Treatment 3C | Treatment 3D |
|---|---|---|---|---|
| 0 | 0.0069 | 0.0125 | 0.0741 | 0.0000 |
| 0.25 | | | 0.7258 | 0.4918 |
| 0.5 | 0.5080 | 0.1879 | 1.2933 | 0.5972 |
| 0.75 | | | 1.3217 | 0.7877 |
| 1 | 1.0233 | 0.4830 | 1.1072 | 0.8080 |
| 1.25 | | | 1.0069 | 0.7266 |
| 1.5 | 1.1062 | 0.7456 | 0.8494 | 0.7001 |
| 1.75 | | | 0.7511 | 0.6472 |
| 2 | 1.0351 | 0.7898 | 0.6554 | 0.5758 |
| 3 | 0.9143 | 0.7619 | 0.6196 | 0.5319 |
| 4 | 0.8522 | 0.7607 | 0.4822 | 0.5013 |
| 5 | 0.8848 | 0.8548 | 0.3875 | 0.4448 |
| 6 | 0.7101 | 0.7006 | 0.3160 | 0.3451 |
| 8 | 0.5421 | 0.5681 | 0.2525 | 0.2616 |
| 10 | 0.4770 | 0.5262 | 0.2361 | 0.2600 |
| 12 | 0.4509 | 0.4454 | 0.2329 | 0.2431 |
| 14 | 0.4190 | 0.4399 | 0.2411 | 0.2113 |
| 16 | 0.4321 | 0.4230 | 0.2385 | 0.2086 |
| 20 | 0.3956 | 0.4240 | 0.2234 | 0.1984 |
| 24 | 0.4526 | 0.4482 | 0.2210 | 0.2135 |
| 30 | 0.4499 | 0.4708 | | |
| 36 | 0.3587 | 0.3697 | 0.1834 | 0.1672 |
| 48 | 0.3023 | 0.3279 | | |

TABLE 18

Pharmacokinetic Parameters of Plasma 6-Hydroxyoxymorphone for Study 3

| | Treatment 3A | | Treatment 3B | | Treatment 3C | | Treatment 3D | |
|---|---|---|---|---|---|---|---|---|
| | Mean | SD | Mean | SD | Mean | SD | Mean | SD |
| $C_{max}$ | 1.2687 | 0.5792 | 1.1559 | 0.4848 | 1.5139 | 0.7616 | 0.9748 | 0.5160 |
| $T_{max}$ | 3.61 | 7.17 | 5.20 | 9.52 | 0.880 | 0.738 | 1.30 | 1.04 |
| $AUC_{(0-t)}$ | 22.47 | 10.16 | 22.01 | 10.77 | 10.52 | 4.117 | 9.550 | 4.281 |
| $AUC_{(0-inf)}$ | 38.39 | 23.02 | 42.37 | 31.57 | 20.50 | 7.988 | 23.84 | 11.37 |
| $T_{1/2el}$ | 39.1 | 36.9 | 39.8 | 32.6 | 29.3 | 12.0 | 44.0 | 35.00 |

Study 4—Controlled Release 20 mg vs Immediate Release 10 mg

A study was conducted to compare the bioavailability and pharmacokinetics of controlled release and immediate release oxymorphone tablets under single-dose and multiple-dose (steady state) conditions. For the controlled release study, healthy volunteers received a single dose of a 20 mg controlled release oxymorphone table on the morning of Day 1. Beginning on the morning of Day 3, the volunteers were administered a 20 mg controlled release oxymorphone tablet every 12 hours through the morning dose of Day 9. For the immediate release study, healthy volunteers received a single 10 mg dose of an immediate release oxymorphone tablet on the morning of Day 1. On the morning of Day 3, additional 10 mg immediate release tablets were administered every six hours through the first two doses on Day 9.

Figure 9:
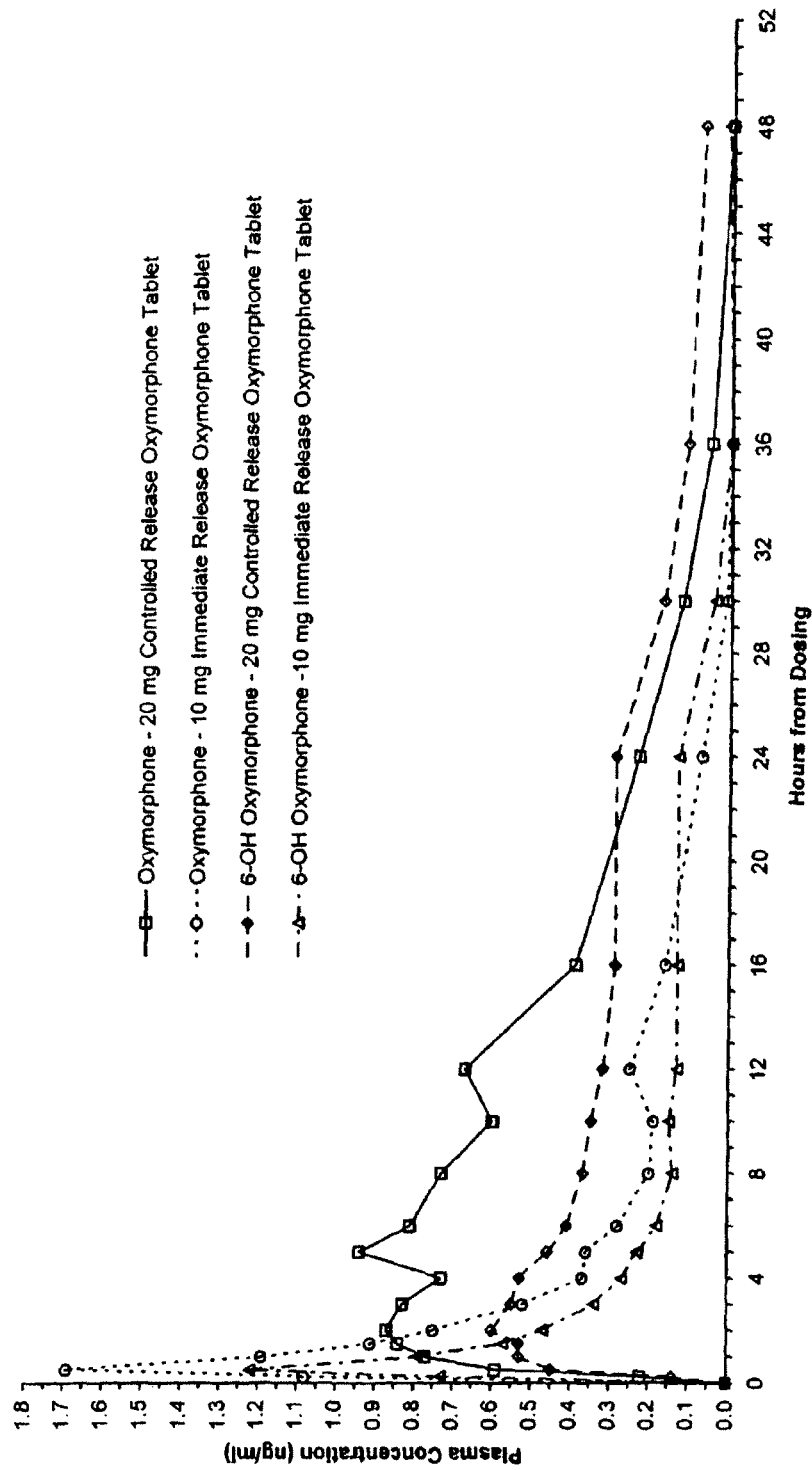
FIG. 9 is a graph of the mean blood plasma concentration of oxymorphone for immediate and controlled release tablets from a single dose study.

FIG. 9 shows the average plasma concentrations of oxymorphone and 6-hydroxyoxymorphone for all subjects after a single dose either controlled release (CR) 20 mg or immediate release (IR) 10 mg oxymorphone. The data in the figure (as with the other relative experimental data herein) is normalized to a 20 mg dose. The immediate release tablet shows a classical curve, with a high, relatively narrow peak followed by an exponential drop in plasma concentration. The controlled release oxymorphone tablets show a lower peak with extended moderate levels of oxymorphone and 6-hydroxy oxymorphone. Table 19 shows the levels of oxymorphone and 6-hydroxy oxymorphone from FIG. 9 in tabular form.

TABLE 19

Mean Plasma Concentration (ng/ml)

| | Oxymorphone | | 6-Hydroxyoxymorphone | |
| --- | --- | --- | --- | --- |
| Hour | Controlled Release 20 mg | Immediate Release 10 mg | Controlled Release 20 mg | Immediate Release 10 mg |
| 0.00 | 0.00 | 0.00 | 0.00 | 0.00 |
| 0.25 | 0.22 | 1.08 | 0.14 | 0.73 |
| 0.50 | 0.59 | 1.69 | 0.45 | 1.22 |
| 1.00 | 0.77 | 1.19 | 0.53 | 0.79 |
| 1.50 | 0.84 | 0.91 | 0.53 | 0.57 |
| 2.00 | 0.87 | 0.75 | 0.60 | 0.47 |
| 3.00 | 0.83 | 0.52 | 0.55 | 0.34 |
| 4.00 | 0.73 | 0.37 | 0.53 | 0.27 |
| 5.00 | 0.94 | 0.36 | 0.46 | 0.23 |
| 6.00 | 0.81 | 0.28 | 0.41 | 0.18 |
| 8.00 | 0.73 | 0.20 | 0.37 | 0.14 |
| 10.0 | 0.60 | 0.19 | 0.35 | 0.15 |
| 12.0 | 0.67 | 0.25 | 0.32 | 0.13 |
| 16.0 | 0.39 | 0.16 | 0.29 | 0.13 |
| 24.0 | 0.23 | 0.07 | 0.29 | 0.13 |
| 30.0 | 0.12 | 0.01 | 0.17 | 0.04 |
| 36.0 | 0.05 | 0.00 | 0.11 | 0.00 |
| 48.0 | 0.00 | 0.00 | 0.07 | 0.01 |

Figure 10:
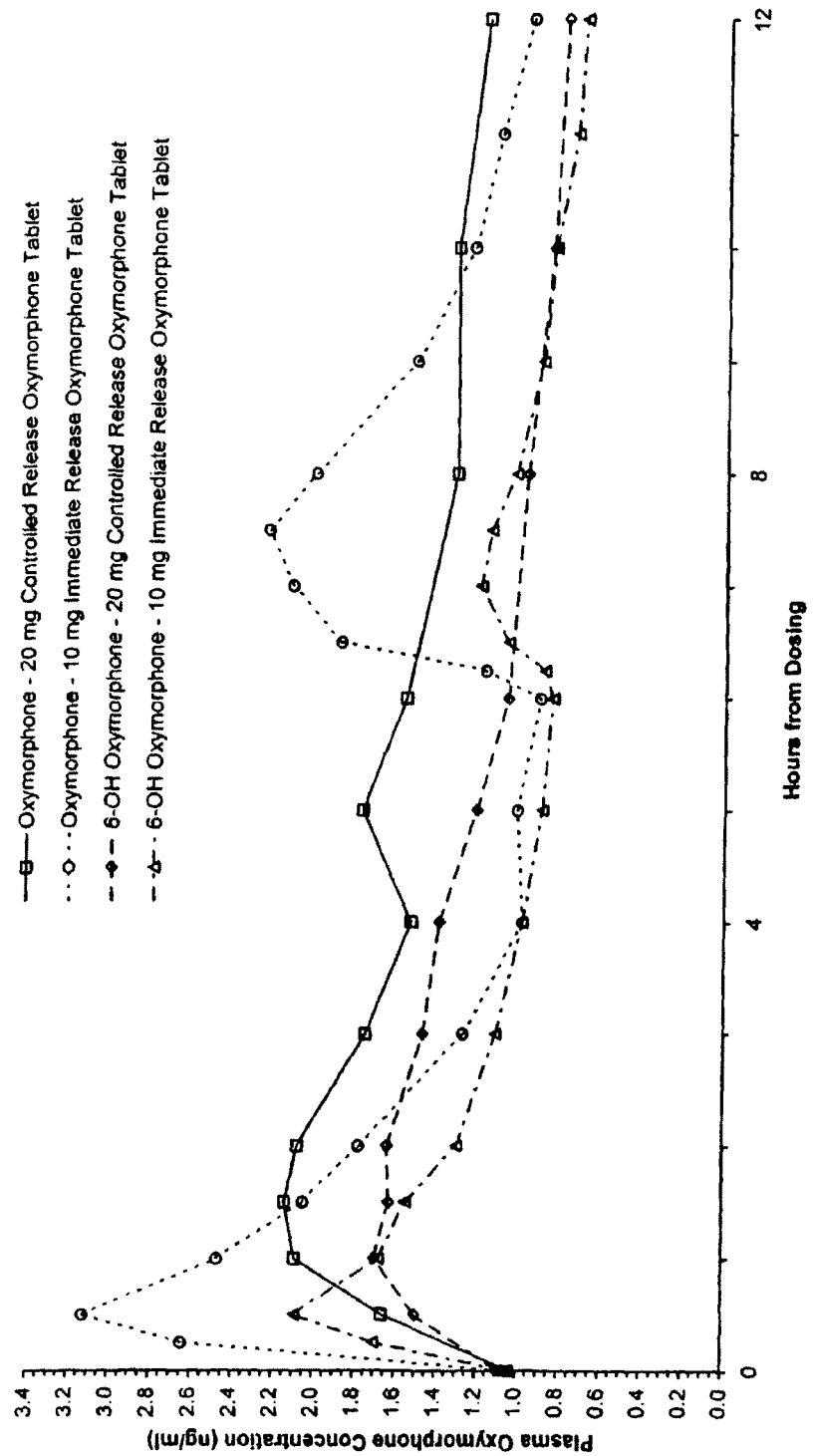
FIG. 10 is a graph of the mean blood plasma concentration of oxymorphone for immediate and controlled release tablets from a steady state study.

FIG. 10 shows the average plasma concentrations of oxymorphone and 6-hydroxyoxymorphone for all subjects in the steady state test, for doses of controlled release 20 mg tablets and immediate release 10 mg tablets of oxymorphone. The figure shows the plasma concentrations after the final controlled release tablet is given on Day 9, and the final immediate release tablet is given 12 hours thereafter. The steady state administration of the controlled release tablets clearly shows a steady moderate level of oxymorphone ranging from just over 1 ng/ml to almost 1.75 ng/ml over the course of a twelve hour period, where the immediate release tablet shows wide variations in blood plasma concentration. Table 20 shows the levels of oxymorphone and 6-hydroxyoxymorphone from FIG. 10 in tabular form.

TABLE 20

Summary of Mean Plasma Concentration (ng/ml)

| | | Oxymorphone | | 6-Hydroxyoxymorphone | |
| --- | --- | --- | --- | --- | --- |
| Day | Hour | Controlled Release 20 mg | Immediate Release 10 mg | Controlled Release 20 mg | Immediate Release 10 mg |
| 4 | 0.00 | 1.10 | 0.75 | 0.89 | 0.72 |
| 5 | 0.00 | 1.12 | 0.84 | 1.15 | 0.88 |
| 6 | 0.00 | 1.20 | 0.92 | 1.15 | 0.87 |
| 7 | 0.00 | 1.19 | 0.91 | 1.27 | 1.00 |
| 8 | 0.00 | 1.19 | 0.86 | 1.29 | 0.98 |
| 9 | 0.00 | 1.03 | 1.07 | 1.09 | 1.05 |
| | 0.25 | | 2.64 | | 1.70 |
| | 0.50 | | 3.12 | 1.50 | 2.09 |
| | 1.00 | | 2.47 | 1.70 | 1.68 |
| | 1.50 | | 2.05 | 1.63 | 1.55 |
| | 2.00 | | 1.78 | 1.64 | 1.30 |
| | 3.00 | | 1.27 | 1.47 | 1.11 |
| | 4.00 | | 0.98 | 1.39 | 0.98 |
| | 5.00 | | 1.01 | 1.21 | 0.89 |
| | 6.00 | | 0.90 | 1.06 | 0.84 |
| | 6.25 | | 1.17 | | 0.88 |
| | 6.50 | | 1.88 | | 1.06 |
| | 7.00 | | 2.12 | | 1.20 |
| | 7.50 | | 2.24 | | 1.15 |
| | 8.00 | 1.32 | 2.01 | 0.97 | 1.03 |
| | 9.00 | | 1.52 | | 0.90 |
| | 10.0 | 1.32 | 1.24 | 0.85 | 0.84 |
| | 11.0 | | 1.11 | | 0.74 |
| | 12.0 | 1.18 | 0.96 | 0.79 | 0.70 |

TABLE 21

Mean Single-Dose Pharmacokinetic Results

| | Controlled Release 20 mg | | Immediate Release 10 mg | |
| --- | --- | --- | --- | --- |
| | oxymorphone | 6-OH-oxymorphone | oxymorphone | 6-OH-oxymorphone |
| $AUC_{(0-t)}$ | 14.74 | 11.54 | 7.10 | 5.66 |
| $AUC_{(0-inf)}$ | 15.33 | 16.40 | 7.73 | 8.45 |
| $C_{max}$(ng/ml) | 1.12 | 0.68 | 1.98 | 1.40 |
| $T_{max}$(hr) | 5.00 | 2.00 | 0.50 | 0.50 |
| $T^{1/2}$(hr) | 9.25 | 26.09 | 10.29 | 29.48 |

Parent 6-OH oxymorphone $AUC_{(o-t)}$ values were lower than the parent compound after administration of either dosage form, but the $AUC_{(o-inf)}$ values are slightly higher due to the longer half-life for the metabolite. This relationship was similar for both the immediate-release (IR) and controlled release (CR) dosage forms. As represented by the average plasma concentration graph, the CR dosage form has a significantly longer time to peak oxymorphone concentration and a lower peak oxymorphone concentration. The 6-OH oxymorphone peak occurred sooner than the parent peak following the CR dosage form, and simultaneously with the parent peak following the IR dosage form.

It is important to note that while the present invention is described and exemplified using 20 mg tablets, the invention may also be used with other strengths of tablets. In each strength, it is important to note how a 20 mg tablet of the same composition (except for the change in strength) would act. The blood plasma levels and pain intensity information are provided for 20 mg tablets, however the present invention is also intended to encompass 5 to 80 mg controlled release tablets. For this reason, the blood plasma level of oxymorphone or 6-hydroxyoxymorphone in nanograms per milliliter of blood, per mg oxymorphone (ng/mg·ml) administered is measured. Thus at 0.02 ng/mg·ml, a 5 mg tablet should produce a minimum blood plasma concentration of 0.1 ng/ml. A stronger tablet will produce a higher blood plasma concentration of active molecule, generally proportionally. Upon administration of a higher dose tablet, for example 80 mg, the blood plasma level of oxymorphone and 6-OH oxymorphone may more than quadruple compared to a 20 mg dose, although conventional treatment of low bioavailability substances would lead away from this conclusion. If this is the case, it may be because the body can only process a limited amount oxymorphone at one time. Once the bolus is processed, the blood level of oxymorphone returns to a proportional level.

It is the knowledge that controlled release oxymorphone tablets are possible to produce and effective to use, which is most important, made possible with the high bioavailability of oxymorphone in a controlled release tablet. This also holds true for continuous periodic administration of controlled release formulations. The intent of a controlled release opioid formulation is the long-term management of pain. Therefore, the performance of a composition when administered periodically (one to three times per day) over several days is important. In such a regime, the patient reaches a "steady state" where continued administration will produce the same results, when measured by duration of pain relief and blood plasma levels of pharmaceutical. Such a test is referred to as a "steady state" test and may require periodic administration over an extended time period ranging from several days to a week or more. Of course, since a patient reaches steady state in such a test, continuing the test for a longer time period should not affect the results. Further, when testing blood plasma levels in such a test, if the time period for testing exceeds the interval between doses, it is important the regimen be stopped after the test is begun so that observations of change in blood level and pain relief may be made without a further dose affecting these parameters.

Study 5—Controlled Release 40 mg vs Immediate Release 4.times.10 mg under Fed and Fasting Conditions The objectives of this study were to assess the relative bioavailability of oxymorphone from oxymorphone controlled release (40 mg) compared to oxymorphone immediate release (4.times.10 mg) under both fasted and fed conditions, and to determine the effect of food on the bioavailability of oxymorphone from the controlled release formulation, oxymorphone CR, and from the immediate release formulation, oxymorphone IR.

This study had a single-center, open-label, analytically blinded, randomized, four-way crossover design. Subjects randomized to Treatment 5A and Treatment 5C, as described below, were in a fasted state following a 10-hour overnight fast. Subjects randomized to Treatment 5B and Treatment 5D, as described below, were in the fed state, having had a high fat meal, completed ten minutes prior to dosing. There was a 14-day washout interval between the four dose administrations. The subjects were confined to the clinic during each study period. Subject assigned to receive Treatment 5A and Treatment 5B were discharged from the clinic on Day 3 following the 48-hour procedures, and subjects assigned to receive Treatment 5C and Treatment 5D were discharged from the clinic on Day 2 following the 36-hour procedures. On Day 1 of each study period the subjects received one of four treatments:

Treatments 5A and 5B: Oxymorphone controlled release 40 mg tablets from Table 2. Subjects randomized to Treatment 5A received a single oral dose of one 40 mg oxymorphone controlled release tablet taken with 240 ml of water after a 10-hour fasting period. Subjects randomized to Treatment 5B received a single oral dose of one 40 mg oxymorphone controlled release tablet taken with 240 ml of water 10 minutes after a standardized high fat meal.

Treatments 5C and 5D: Immediate release tablet (IR) 4.times.10 mg Oxymorphone. Subjects randomized to Treatment 5C received a single oral dose of 4.times.10 mg oxymorphone IR tablet taken with 240 ml of water after a 10-hour fasting period. Subjects randomized to Treatment 5D received a single oral dose of 4.times.10 mg oxymorphone IR tablet taken with 240 ml of water 10 minutes after a standardized high-fat meal.

A total of 28 male subjects were enrolled in the study, and 25 subjects completed the study. A total of 28 subjects received at least one treatment. Only subjects who completed all 4 treatments were included in the summary statistics and statistical analysis.

Blood samples (7 ml) were collected during each study period at the 0 hour (predose), and at 0.25, 0.5, 0.75, 1.0, 1.5, 2, 3, 4, 5, 6, 8, 10, 12, 24, 36, 48, 60, and 72 hours post-dose (19 samples) for subjects randomized to all Treatments.

The mean oxymorphone plasma concentration versus time is presented in Table 22. The arithmetic means of the plasma oxymorphone pharmacokinetic parameters and the statistics for all Treatments are summarized in Table 23.

TABLE 22

Mean Plasma Concentration vs. Time (ng/ml)

| Time (hr) | Treatment 5A | Treatment 5B | Treatment 5C | Treatment 5D |
|---|---|---|---|---|
| 0 | 0.00 | 0.00 | 0.00 | 0.00 |
| 0.25 | 0.47 | 0.22 | 3.34 | 1.79 |
| 0.50 | 1.68 | 0.97 | 7.28 | 6.59 |
| 0.75 | 1.92 | 1.90 | 6.60 | 9.49 |
| 1 | 2.09 | 2.61 | 6.03 | 9.91 |
| 1.5 | 2.18 | 3.48 | 4.67 | 8.76 |
| 2 | 2.18 | 3.65 | 3.68 | 7.29 |
| 3 | 2.00 | 2.86 | 2.34 | 4.93 |
| 4 | 1.78 | 2.45 | 1.65 | 3.11 |
| 5 | 1.86 | 2.37 | 1.48 | 2.19 |
| 6 | 1.67 | 2.02 | 1.28 | 1.71 |
| 8 | 1.25 | 1.46 | 0.92 | 1.28 |
| 10 | 1.11 | 1.17 | 0.78 | 1.09 |
| 12 | 1.34 | 1.21 | 1.04 | 1.24 |
| 24 | 0.55 | 0.47 | 0.40 | 0.44 |
| 36 | 0.21 | 0.20 | 0.16 | 0.18 |
| 48 | 0.06 | 0.05 | 0.04 | 0.05 |
| 60 | 0.03 | 0.01 | 0.01 | 0.01 |
| 72 | 0.00 | 0.00 | 0.00 | 0.00 |

TABLE 23

Pharmacokinetic Parameters of Plasma Oxymorphone for Study 5

| | Treatment 5A | | Treatment 5B | | Treatment 5C | | Treatment 5D | |
|---|---|---|---|---|---|---|---|---|
| | Mean | SD | Mean | SD | Mean | SD | Mean | SD |
| $C_{max}$ | 2.79 | 0.84 | 4.25 | 1.21 | 9.07 | 4.09 | 12.09 | 5.42 |
| $T_{max}$ | 2.26 | 2.52 | 1.96 | 1.06 | 0.69 | 0.43 | 1.19 | 0.62 |
| $AUC_{(0-t)}$ | 35.70 | 10.58 | 38.20 | 11.04 | 36.00 | 12.52 | 51.35 | 20.20 |
| $AUC_{(0-inf)}$ | 40.62 | 11.38 | 41.17 | 10.46 | 39.04 | 12.44 | 54.10 | 20.26 |
| $T_{1/2el}$ | 12.17 | 7.57 | 10.46 | 5.45 | 11.65 | 6.18 | 9.58 | 3.63 |

The relative bioavailability calculations are summarized in Tables 24 and 25.

TABLE 24

Relative Bioavailability Determination Based on $AUC_{(0-inf)}$

| $F_{rel}$ (5D vs. 5C) | $F_{rel}$ (5B vs. 5A) |
|---|---|
| 1.3775 | 1.0220 |

TABLE 25

Relative bioavailability Determination Based on $AUC_{(0-24)}$

| $F_{rel}$ (5D vs. 5C) | $F_{rel}$ (5B vs. 5A) |
|---|---|
| 1.4681 | 1.0989 |

The mean 6-OH oxymorphone plasma concentration versus time is presented in Table 26.

TABLE 26

Mean Plasma Concentration vs. Time (ng/ml)
6-Hydroxyoxymorphone

| Time (hr) | Treatment 5A | Treatment 5B | Treatment 5C | Treatment 5D |
|---|---|---|---|---|
| 0 | 0.00 | 0.00 | 0.00 | 0.00 |
| 0.25 | 0.27 | 0.05 | 2.36 | 0.50 |
| 0.50 | 1.32 | 0.31 | 5.35 | 1.98 |
| 0.75 | 1.37 | 0.59 | 4.53 | 2.97 |
| 1 | 1.44 | 0.82 | 3.81 | 2.87 |
| 1.5 | 1.46 | 1.09 | 2.93 | 2.58 |
| 2 | 1.46 | 1.28 | 2.37 | 2.29 |
| 3 | 1.39 | 1.14 | 1.69 | 1.72 |
| 4 | 1.25 | 1.14 | 1.33 | 1.26 |
| 5 | 1.02 | 1.00 | 1.14 | 1.01 |
| 6 | 0.93 | 0.86 | 0.94 | 0.86 |
| 8 | 0.69 | 0.72 | 0.73 | 0.77 |
| 10 | 0.68 | 0.67 | 0.66 | 0.75 |
| 12 | 0.74 | 0.66 | 0.70 | 0.77 |
| 24 | 0.55 | 0.52 | 0.54 | 0.61 |
| 36 | 0.23 | 0.30 | 0.28 | 0.27 |
| 48 | 0.18 | 0.20 | 0.20 | 0.19 |
| 60 | 0.09 | 0.10 | 0.09 | 0.09 |
| 72 | 0.06 | 0.06 | 0.04 | 0.05 |

TABLE 27

Pharmacokinetic Parameters of Plasma
6-Hydroxyoxymorphone for Study 5

| | Treatment 5A | | Treatment 5B | | Treatment 5C | | Treatment 5D | |
|---|---|---|---|---|---|---|---|---|
| | Mean | SD | Mean | SD | Mean | SD | Mean | SD |
| $C_{max}$ | 1.88 | 0.69 | 1.59 | 0.63 | 6.41 | 3.61 | 3.79 | 1.49 |
| $T_{max}$ | 1.48 | 1.18 | 2.73 | 1.27 | 0.73 | 0.47 | 1.18 | 0.74 |
| $AUC_{(0-t)}$ | 28.22 | 10.81 | 26.95 | 11.39 | 33.75 | 10.29 | 32.63 | 13.32 |
| $AUC_{(0-inf)}$ | 33.15 | 11.25 | 32.98 | 10.68 | 37.63 | 17.01 | 36.54 | 13.79 |
| $T_{1/2el}$ | 17.08 | 7.45 | 21.92 | 8.41 | 16.01 | 6.68 | 16.21 | 7.42 |

Example 5

Study Objectives

The objective of this study was to determine the effect of renal impairment on the pharmacokinetics and metabolism of oxymorphone following a single oral dose of EN3202 (oxymorphone HCl extended-release) tablets.

Methods

Clinical Study Design and Conduct

This study employed a single-dose, parallel-group study design in 24 subjects with chronic renal insufficiency (8 with mild renal impairment, creatinine clearance=51-80 mL/min; 8 with moderate renal impairment, creatinine clearance=30-50 mL/min; and 8 with severe renal impairment, creatinine clearance <30 mL/min.) and 8 healthy controls with normal renal function (creatinine clearance >80 mL/min). Attempts were made to match controls with the renal impaired patients with respect to age, gender, and weight. Each subject received a single 20 mg dose of EN3202 (oxymorphone ER). The oxymorphone ER tablets administered were according to the now-available commercial formula of Opana® 20 mg strength, which also contains the inactive ingredients hypromellose, iron oxide black, methylparaben, propylene glycol, silicified microcrystalline cellulose, sodium stearyl fumarate, TIMERx®-N, titanium dioxide, triacetin, FD&C blue No. 1, FD&C yellow No. 6, and FD&C yellow No. 10. Naltrexone (50 mg) was administered on the evening prior to administration of the EN3202 dose. Plasma and urine were collected for 120 hours after the administration of EN3202 to determine oxymorphone and metabolite concentrations. Study participants were housed in the clinical research facility during the treatment period, beginning on the evening prior to administration of the test medication and extending until collection of the 120-hr blood sample and urine collection following dose administration.

1.1.1 Overall Study Design

The study procedures are outlined in the following table (Table 28).

TABLE 28

Schedule of Study Evaluations

| Phase | Screening | Treatment Period | | | | | |
|---|---|---|---|---|---|---|---|
| VISIT NUMBER | 1 | 2 | | | | | |
| DAY | −21 | −1 | 1 | 2 | 3 | 4 | 5 | 6 |
| Medical/Medication History | X | | | | | | | |
| Informed Consent | X | | | | | | | |
| Assessment of Eligibility | X | X | | | | | | |
| Physical Examination | X | | | | | | | X |
| 12-lead Electrocardiogram | X | | | | | | | |
| Clinical Laboratory Tests | X | | | | | | | X |
| Serum HCG* | X | | | | | | | |
| Vital Signs | X | | X | X | X | X | X | X |
| Body Weight | X | | | | | | | |
| Clinic Check-in | | X | | | | | | |
| Clinic Discharge | | | | | | | | X |
| Urine Pregnancy Test* | | X | | | | | | |
| Urine Drug Screen | X | X | | | | | | |
| Naltrexone Dose | | X | | | | | | |
| EN3202 Dose | | | X | | | | | |
| Plasma Samples | | | a | a | a | a | a | a |
| Urine Collection | | | b | b | b | b | b | b |
| Assessment of AEs | | | X | X | X | X | X | X |

<sup>a</sup>Plasma sample times: 0 (pre-dose), 0.5, 1.0, 1.5, 2.0, 3.0, 4.0, 5.0, 6.0, 8.0, 10.0, 12.0, 18.0, 24, 30, 36, 48, 60, 72, 84, 96, 108, and 120 hours after dose administration.
<sup>b</sup>Urine collection times: 0 (pre-dose), 0-12, 12-24, 24-48, 48-72, 72-96, 96-120 hours after dose administration.
*For women of childbearing potential.

A series of screening evaluations were performed to determine whether prospective study participants met the selection criteria for the trial. Screening evaluations were performed within a 21-day period prior to receiving the study medication. Screening evaluations consisted of a medical history and review of systems, medication history, physical examination, 12-lead electrocardiogram, laboratory evaluations, and urine drug screen. A serum pregnancy test was obtained for women of childbearing potential. Screening tests for hepatitis and HIV infection were obtained only at the screening visit.

Creatinine clearance ($Cl_{CR}$) was estimated at screening using the following Cockroft and Gault[8] equation:

$$Cl_{CR} = \frac{(140 - \text{age}) \cdot (BW)}{(72 \times S_{CR})} \text{(for males; female = male} \times 0.85)$$

Where:
$S_{CR}$=serum creatinine (mg/dL)
BW=body weight in kg
Age=age in years

Urine drug screens were performed during screening and upon admission to the clinic on the day prior to the treatment period. Urine pregnancy tests were performed at check-in (when applicable). Each subject's continuing eligibility (e.g., inclusion and exclusion criteria, concomitant medications, etc.) was verified at check-in. Routine vital signs, including pulse, respiratory rate, blood pressure, and temperature were obtained in conjunction with the screening physical examination, just prior to administration of the test medication, and at 24, 48, 72, 96, and 120 hours after administration of the test medication. Blood pressure and pulse were obtained with the subject in the sitting position after sitting for 5 minutes. Laboratory evaluations, physical examinations, and vital sign measurements were repeated at the conclusion of the treatment period. Additional vital signs were to be obtained when clinically indicated.

Any significant abnormalities were to be fully investigated. Laboratory results with significantly abnormal values were to be repeated for verification. Additional tests and other evaluations required to establish the significance or etiology of an abnormal result or to monitor the course of an adverse event were to be obtained when clinically indicated. In particular, if a clinically significant abnormal result was observed that was not resolved by the final study visit, repeat tests were to be performed to document resolution or stability of the abnormality. Any additional relevant data obtained by the investigator during the course of this study were to be supplied to the sponsor.

At the screening visit, subjects were informed not to take any medications (prescription or OTC) until the study began. Renally impaired subjects were allowed to take approved prescribed concomitant medications. The investigator informed each prospective subject of the nature of the study, explained the potential risks, and obtained written informed consent from the subject prior to performing any procedures involving more than minimal risk and prior to the administration of study medication.

Study participants reported to the clinic on the day prior to dose administration (time specified by the investigator) and remained in the clinic until released by the investigator subsequent to obtaining the 120-hour blood sample and urine collection. Naltrexone (50 mg) was administered on the evening prior to administration of EN3202 dose. While in the clinic, the subjects refrained from strenuous physical activity. Subjects fasted from approximately 22:00 on the evening prior to dose administration until four (4) hours after dose administration. At the end of the fasting period, the subjects received a standard diet for the remainder of their time in the clinic. The subjects were not to receive any xanthine-containing foods or beverages.

This was a single-dose trial. As a result, any subject who received the dose of test medication remained in the trial and completed all required tests and evaluations unless: a) the subject withdrew his or her consent for further participation; b) the investigator determined that continued participation in the trial placed the subject at unacceptable risk; or c) the investigator determined that the subject required medical treatment that could not be administered at the study facility.

Subjects who withdrew from the study prior to completion of the study evaluations and blood samples scheduled for 72 hours following dose administration could be replaced. Plasma samples could not be analyzed for subjects who discontinued from the trial prior to collection of the 72-hour blood sample. If a subject withdrew from the study, the investigator was to contact the monitor to discuss the necessity of replacement, and the decision was to be made prior to the analysis of plasma samples. The replacement subject was to match the population of the subject that was withdrawn (i.e., healthy control, or renally impaired).

The date the subject withdrew from the study and the reason for discontinuation were to be recorded on the case report form. When a subject withdrew from the study (regardless of the reason), all evaluations required at the final study visit were to be performed.

Selection of the Study Population

A total of 34 subjects were enrolled in the trial, and 32 subjects completed the trial with 8 subjects in each of the following four (4) treatment groups:

| Group | Creatinine Clearance* |
|---|---|
| Controls | >80 mL/min |
| Mild Renal Impairment | 51 to 80 mL/min |
| Moderate Renal Impairment | 30 to 50 mL/min |
| Severe Renal Impairment | <30 mL/min |

*Estimated using the method of Cockroft and Gault.

A total of 36 subjects could be enrolled to allow for the completion of 32 subjects.

To prevent the occurrence of acute abstinence syndrome resulting from naltrexone administration, the investigator carefully screened potential study participants to ensure that no reasonable possibility of recent or prolonged opioid use or abuse existed. All potential study participants were informed of the risks associated with attempting to withhold any history of recent opioid use.

Subjects with Chronic Renal Insufficiency

Inclusion Criteria:

Twenty-six (26) male or female subjects with chronic renal insufficiency were enrolled based on the following criteria:

Male or nonpregnant female 18 years of age or older. Female patients of childbearing potential must have had a negative serum β-hCG level consistent with nongravid state at the pre-study screening visit and agreed to use an appropriate method of contraception.

Diagnosis of chronic (≥6 months) renal insufficiency due to any etiology that had been clinically stable (without episodes of acute renal failure, fluctuating serum creatinine, or required dialysis) for the last 2 months.

Estimated creatinine clearance within the range of 51 to 80 mL/min (8 subjects), 30 to 50 mL/min (8 subjects), or <30 mL/min (8 subjects).

Body weights not less than 110 lb and within 30% of the Metropolitan Life Insurance Company's standards dated 1983.

Able to communicate effectively with study personnel.

Hemoglobin ≥10 g/dL.

Platelet count >50,000 cells/□L.

Normal 12-lead electrocardiogram without any clinically significant abnormalities of rate, rhythm, or conduction.

Adequately informed of the nature and risks of the study and have given written informed consent prior to receiving study medication.

Exclusion Criteria:

Any of the following conditions were cause for exclusion from the study:

Known hypersensitivity or allergy to oxymorphone or naltrexone.

Any disease or condition (medical or surgical) other than those relating to their renal disease that might compromise the hematologic, cardiovascular, pulmonary, hepatic, gastrointestinal, or central nervous system.

Presence of significant abnormalities other than those related to their renal insufficiency in pre-study clinical examination or laboratory measurements.

Inadequately controlled hypertension, defined as diastolic blood pressure >100 mmHg.

Positive screen for either Hepatitis B (Hepatitis B Surface Antigen) or HIV.

Received an investigational drug within a period of 30 days prior to enrollment in the study; consumption of alcohol within 72 hours prior to study initiation; or use of an unacceptable concomitant medication.

Positive urine drug screen, including ethanol, cocaine, THC, barbiturates, amphetamines, benzodiazepines, and opiates.

Any history of alcohol abuse, illicit drug use, significant mental illness, physical dependence to any opioid, or any history of drug abuse or addiction.

A history of difficulty with donating blood.

Received the study medication previously.

Healthy Control Subjects

Inclusion Criteria:

Eight (8) healthy controls subjects were enrolled based on the following criteria:

Male or nonpregnant female 18 years of age or older. Female patients of childbearing potential must have had a negative serum β-hCG level consistent with nongravid state at the pre-study screening visit and agreed to use an appropriate method of contraception.

Body weights not less than 110 lb and within 30% of the Metropolitan Life Insurance Company's standards dated 1983.

Able to communicate effectively with the study personnel.

Estimated creatinine clearance >80 mL/min.

No significant disease or abnormal laboratory values as determined by medical history, physical examination, or laboratory evaluations conducted at the screening visit or on admission to the clinic.

Normal 12-lead electrocardiogram without any clinically significant abnormalities of rate, rhythm, or conduction.

Adequately informed of the nature and risks of the study and have give written informed consent prior to receiving study medication.

Exclusion Criteria:

Any of the following conditions are cause for exclusion from the study:

Known hypersensitivity or allergy to oxymorphone or naltrexone.

Any disease or condition (medical or surgical) that might compromise the hematologic, cardiovascular, pulmonary, renal, gastrointestinal, hepatic, or central nervous system, or other conditions that might interfere with the absorption, distribution, metabolism, or excretion of the study drug or place the subject at increased risk.

Presence of abnormal laboratory values that are considered clinically significant. In addition, no subject with liver enzymes (SGOT or SGPT) above 1.25 times the upper limit of normal, total bilirubin above the upper limit of normal, serum creatinine above the upper limit of normal, or tests of hematologic function (hemoglobin, hematocrit, white blood cells or platelets) below the lower limit of normal were to be admitted to the study.

Positive screen for either Hepatitis B (Hepatitis B Surface Antigen) or HIV.

Received an investigational drug within a period of 30 days prior to enrollment in the study. Any prescription drug therapy within 2 weeks of initiation of the study. This exclusion was extended to 4 weeks for any drugs known to affect hepatic drug metabolism. No non-prescription (OTC) drugs were to be taken within 24 hours of admission into the study. No consumption of alcohol within 72 hours prior to study initiation.

Positive urine drug screen including ethanol, cocaine, THC, barbiturates, amphetamines, benzodiazepines, and opiates.

Any history of alcohol abuse, illicit drug use, significant mental illness, physical dependence to any opioid, or any history of drug abuse or addiction.

A history of difficulty with donating blood.

Received the study medication previously.

Concomitant Medications

Healthy Control Subjects

Could not use concomitant prescription medications during the study period beginning 2 weeks prior to the first dose (4 weeks for any drug that might affect hepatic drug metabolism [see Appendix F of the study protocol]).

Could not take OTC medications during the study beginning 24 hours prior to the administration of the test medication without prior authorization of the investigator.

Could not consume alcoholic beverages during the study beginning 72 hours prior to the administration of the test medication.

Renally Impaired Subjects

Could continue to receive all medications chronically administered for treatment or maintenance of their disease (such medications must have been administered at a stable dosage for a minimum of 2 weeks prior to entry into the trial).

Could not take OTC medications without prior authorization of the investigator.

Could not consume alcoholic beverages during the study beginning 72 hours prior to administration of the first dose of study medication.

Could receive additional medications, when medically necessary, at the discretion of the investigator.

General Considerations

Opioid analgesics or opioid-containing medications (e.g., cough suppressants containing opioids or dextromethorphan) were to be prohibited beginning 2 weeks prior to the first dose and until the subjects were discharged from the study.

Drugs that affect gastrointestinal motility were not to be administered within 24 hours before or after administration of the test medication. A laxative could be administered if required, but the concurrent administration of any laxative was prohibited within 24 hours before or after administration of the test medication.

Medications with CNS-depressant effects were not to be administered during the course of the study. If the renally impaired subjects required the use of such medications, the medication was to be administered at a stable dosage for a minimum of 2 weeks prior to entry into the study and was to remain at a constant dose throughout the study.

Study Medications

All study medications were supplied by the sponsor. Medications utilized in this trial included the following:

EN3202 (oxymorphone HCl extended-release) tablets 20 mg (test medication). The oxymorphone ER tablets administered were according to the now-available commercial formula of Opana® 20 mg strength, which also contains the inactive ingredients hypromellose, iron oxide black, methylparaben, propylene glycol, silicified microcrystalline cellulose, sodium stearyl fumarate, TIMERx®-N, titanium dioxide, triacetin, FD&C blue No. 1, FD&C yellow No. 6, and FD&C yellow No. 10.

ReVia® (naltrexone HCl) tablets 50 mg (opioid antagonist)

In order to protect the subjects from potential opioid-related adverse events, a single 50-mg dose of the opioid antagonist ReVia® (naltrexone HCl) was administered at 20:00 the evening prior to administration of test medication. A single 20-mg dose of oxymorphone HCl was administered following an overnight fast. Subjects continued fasting until four (4) hours after dose administration. The subjects remained in an upright posture (sitting or standing) for 1 hour after dose administration. All doses were administered with 240 mL of water (room temperature), and the subjects were instructed to drink all the water.

Randomization and Blinding

As participants in this study each received only a single dose of EN3202, a randomization schedule was not required. This study was not subject to blinding.

Safety Assessments

Each subject was carefully monitored for the development of any adverse experiences. This information was obtained in the form of non-leading questions (e.g., "How are you feeling?") and from signs and symptoms detected during each examination, observations of the study personnel, or spontaneous reports from the subjects.

A standard 12-lead electrocardiogram was obtained at screening. Additional electrocardiograms were to be obtained if clinically indicated. A follow-up electrocardiogram was to be obtained if any significant abnormalities were detected after dose administration.

A complete physical examination was performed at the screening visit and at the conclusion of the treatment period. Routine vital signs, including pulse, respiratory rate, blood pressure, and temperature, were obtained at the screening physical examination, just prior to administration of the test medication, and at 24, 48, 72, 96, and 120 hours after administration of the test medication. Blood pressure and pulse were obtained with the subject in a sitting position after sitting for 5 minutes. Additional vital signs were to be obtained when clinically indicated.

A complete series of laboratory evaluations (including blood chemistry, hematology and urinalysis) were obtained during the screening phase and also at the conclusion of the study. Screening tests for hepatitis and HIV infection (and serum pregnancy tests when applicable) were obtained only at the screening visit. Urine drug screens were performed during screening and upon admission to the clinic on the day prior to the treatment period. Urine pregnancy tests were performed at check-in (when applicable).

Any additional relevant data obtained by the investigator during the course of this study were to be supplied to the sponsor.

Analytical Methods

A total of four (4) validated LC/MS/MS methods were utilized to measure the concentrations of oxymorphone, 6-OH-oxymorphone, and oxymorphone-3-glucuronide in plasma and urine samples. The methods include: oxymorphone and 6-OH-oxymorphone in plasma (001005.01); oxymorphone-3-glucuronide in plasma (001107); oxymorphone and 6-OH-oxymorphone in urine (001007.01), and oxymorphone-3-glucuronide in urine (001106). In all methods, the internal standards are d3-oxymorphone, d3-6-OH-oxymorphone, and d3-oxymorphone-3-glucuronide for oxymorphone, 6-OH-oxymorphone, and oxymorphone-3-glucuronide, respectively. The methods for simultaneous determination of oxymorphone and 6-OH-oxymorphone utilize liquid-liquid extraction of plasma or urine; the method for oxymorphone-3-glucuronide utilizes solid phase extraction. Validation results are summarized in the following tables:

TABLE 29

Summary of Method Validation Results for Plasma Analytes

| Parameter | OXM | 6-OH-OXM | OXM-3-G |
| --- | --- | --- | --- |
| Standard Concentrations (ng/mL) | 0.1, 0.2, 0.5, 1, 5, 10, 18, 20 | 0.1, 0.2, 0.5, 1, 5, 10, 18, 20 | 5, 12.5, 25, 50, 125, 200, 250 |
| QC Concentrations (ng/mL) | 0.3, 6, 14 | 0.3, 6, 14 | 15, 75, 180 |
| Linearity (mean r) | 0.9994 | 0.9987 | 0.9982 |
| Linear Range (ng/mL) | 0.1-20 | 0.1-20 | 5-250 |
| LOQ (ng/mL) | 0.1 | 0.1 | 5.0 |
| Intra-day Precision (% CV)* | 1.43-3.93 | 2.12-7.87 | 1.39-6.79 |
| Intra-day Accuracy (% Actual)* | 94.33-96.56 | 98.17-102.56 | 101.00-105.31 |
| Inter-day Precision (% CV)* | 2.86-7.77 | 3.83-7.74 | 3.85-5.53 |
| Inter-day Accuracy (% Actual)* | 97.31-99.36 | 100.36-101.70 | 98.99-102.36 |
| Recovery (%) | 53.98 | 22.96 | 79.30 |

*precision and accuracy results based on QC samples
OXM = oxymorphone
6-OH-OXM = 6-OH-oxymorphone
OXM-3-G = oxymorphone-3-glucuronide

TABLE 30

Summary of Method Validation Results for Urine Analytes

| Parameter | OXM | 6-OH-OXM | OXM-3-G |
|---|---|---|---|
| Standard Concentrations (ng/mL) | 1, 2.5, 10, 25, 50, 100, 150, 200 | 1, 2.5, 10, 25, 50, 100, 150, 200 | 10, 25, 100, 250, 500, 1000, 1500, 2000 |
| QC Concentrations (ng/mL) | 1.5, 60, 140 | 1.5, 60, 140 | 30, 600, 1400 |
| Linearity (mean r) | 0.9994 | 0.9988 | 0.9990 |
| Linear Range (ng/mL) | 1-200 | 1-200 | 10-2000 |
| LOQ (ng/mL) | 1.0 | 1.0 | 10.0 |
| Intra-day Precision (% CV)* | 2.00-7.26 | 3.04-4.73 | 4.63-6.02 |
| Intra-day Accuracy (% Actual)* | 101.89-103.49 | 99.56-103.43 | 99.41-103.59 |
| Inter-day Precision (% CV)* | 3.18-7.04 | 3.73-7.86 | 4.55-6.17 |
| Inter-day Accuracy (% Actual)* | 98.92-102.33 | 98.70-100.65 | 97.50-99.26 |
| Recovery (%) | 62.92 | 67.10 | 78.51 |

*precision and accuracy results based on QC samples
OXM = oxymorphone
6-OH-OXM = 6-OH-oxymorphone
OXM-3-G = oxymorphone-3-glucuronide Pharmacokinetic and Statistical Methods This was a parallel-group trial designed to enroll 24 subjects with mild, moderate, and severe renal impairment (8 subjects for each level of impairment) and 8 healthy control subjects. Groups were matched for age, gender, and weight as closely as possible.

Samples of venous blood were obtained in 7 mL EDTA tubes just prior to dose administration (time 0), and at 0.5, 1.0, 1.5, 2.0, 3.0, 4.0, 5.0, 6.0, 8.0, 10.0, 12.0, 18.0, 24.0, 30.0, 36.0, 48.0, 60.0, 72.0, 84.0, 96.0, 108.0, and 120 hours after dose administration.

Urine samples were obtained for 120 hours after dose administration. Subjects were to be instructed to void just prior to administration of the test medication (time 0) and all urine was to be collected during the intervals of 0-12, 12-24, 24-48, 48-72, 72-96, and 96-120 hours after administration of the test medication. Each subject was to be instructed to void at the end of each interval (so that each collection interval began with an empty bladder). The void prior to administration of the test medication (time 0) served as the pre-dose blank and was not be included in the collection container.

Calculation of Pharmacokinetic Variables

Plasma and urine pharmacokinetic variables were calculated from the concentration data using standard, non-compartmental methods as outlined in the following table.

Statistical Methods

All pharmacokinetic results are summarized using appropriate descriptive statistics. Continuous variables were compared between renally impaired and control groups using appropriate parametric statistics. 90% confidence intervals were calculated for the differences or ratios between the renally impaired and control groups. In addition, the association between oral clearance (and other pharmacokinetic variables) and the severity of renal insufficiency (based on creatinine clearance) was explored.

The frequency of adverse experiences (AEs) were tabulated by MedDRA term and body system. The incidence of AEs is compared across treatment groups using an appropriate non-parametric statistic. The maximum intensity and frequency of AEs are summarized by treatment group. A new-onset AE is defined as an AE that was not present prior to treatment with study medication but appeared following treatment or was present at treatment initiation but worsened during treatment. An AE that was present at treatment initiation but resolved and then reappeared while the patient was on treatment is a new-onset AE (regardless of the intensity of the AE when the treatment was initiated).

All vital sign measurements are summarized by mean values and changes from baseline. Changes from baseline were analyzed across treatment groups using an appropriate parametric statistic.

TABLE 31

Definition of Pharmacokinetic Variables

| Variable | Definition |
|---|---|
| Cmax | Maximum plasma concentration; the highest concentration observed during a dosage interval. |
| Tmax | The time that Cmax was observed. |
| $C_t$ | The last measured plasma concentration; the last concentration above the lower LOQ following a dose. |
| $\lambda_z$ (Ke) | The terminal elimination rate constant; calculated using linear regression on the terminal portion of the Ln-concentration versus time curve. |
| $t\frac{1}{2}$ | Terminal elimination half-life; calculated as $0.693/\lambda z$. |
| AUCT | Area under the concentration versus time curve from time 0 to the last measured concentration ($C_t$); calculated using linear trapezoid rule. |
| AUC | Area under the concentration versus time curve from time 0 to infinity; calculated as $AUCT + C_t/\lambda_z$. |
| CLo | Clearance after oral administration; calculated as dose/AUC. |
| UER | Urinary excretion rate; calculated as the amount excreted during a collection interval (concentration in nmol × volume)/the duration of collection (in hr). |
| $t\frac{1}{2}$UER | Elimination half-life estimated from urinary excretion rate; calculated using linear regression on the terminal portion of the Ln-UER versus time curve, where time is the mid-point of the collection interval. |

Results
Disposition of Subjects

Thirty-four (34) participants, 8 healthy, 9 with mild renal impairment, 8 with moderate renal impairment, and 9 with severe renal impairment were enrolled and received treatment; 32 completed the trial, and 2 subjects discontinued the trial. Of the two subjects who discontinued the trial, one was in the mild renal impairment group (Subject 100), and one was in the severe renal impairment group (Subject 305). Both subjects discontinued due to adverse events.

The study population consisted of 22 men and 12 women ranging from 29 to 87 years of age. As the severity of renal impairment tends to increase with age, the renally impaired subjects were generally older, shorter, and weighed less than the healthy control subjects. The renally impaired subjects were well matched for weight and height. (Table 32).

generally parallel. Examination of FIG. 1 reveals a clear difference in the plasma concentrations of oxymorphone-3-glucuronide across the four treatment groups. The mean plasma oxymorphone concentrations in subjects with renal impairment generally exceeded those in the control group during the first 12 hours after dose administration. As was the case with the 3-glucuronide metabolite, the mean plasma oxymorphone concentrations generally followed the order severe>moderate>mild>control. There was less clear separation in mean 6-OH-oxymorphone between the mild and moderately impaired groups relative to the healthy controls.

Mean (±SD) pharmacokinetic results for oxymorphone, 6-OH-oxymorphone, and oxymorphone-3-glucuronide are summarized by treatment group in Table 33.

TABLE 32

Summary of Demographic Characteristics

|  | Mild Impairment | Moderate Impairment | Severe Impairment | Healthy Controls |
|---|---|---|---|---|
| Number | 9 | 8 | 9 | 8 |
| Males | 3 | 5 | 7 | 7 |
| Females | 6 | 3 | 2 | 1 |
| Age (years)$^a$ | 53.0 (3.83) | 58.3 (5.68) | 63.0 (4.27) | 41.9 (3.09) |
| Height (in)$^a$ | 64.6 (1.32) | 65.8 (0.65) | 66.6 (1.53) | 70.4 (1.44) |
| Weight (lbs)$^a$ | 161.8 (11.68) | 168.9 (9.40) | 166.6 (8.18) | 188.1 (8.11) |
| Creatinine Clearance (mL/min)$^b$ | 63.1 (3.25) | 42.2 (2.07) | 19.8 (1.46) | 103.1 (5.79) |

$^a$Mean (SE)
$^b$Mean (SE) creatinine clearance estimated by method of Cockroft and Gault (ref 8)

Figure 11:
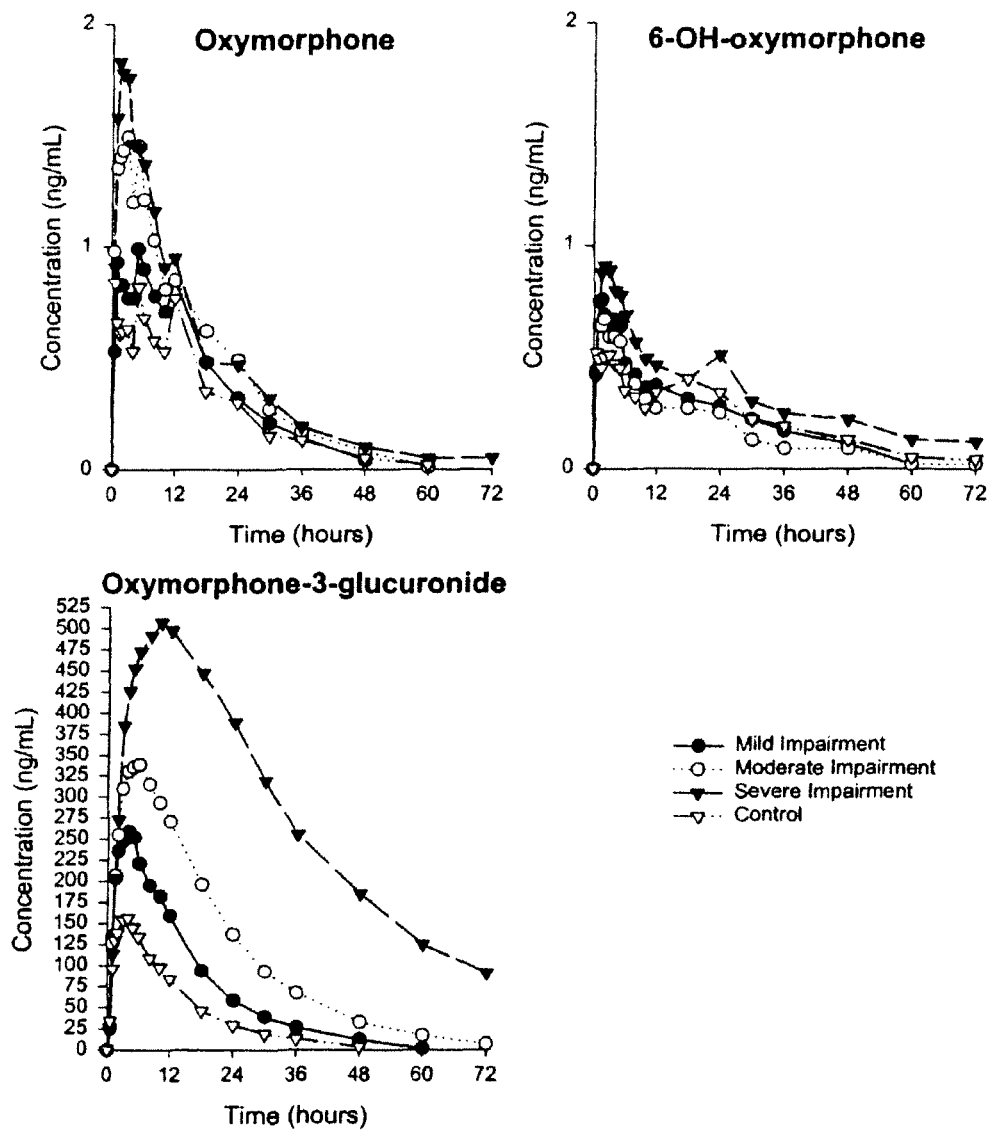
FIG. 11 is a graph of the mean plasma concentration of oxymorphone, 6-OH-oxymorphone, and oxymorphone-3-glucuronide.

Results of Pharmacokinetic and Statistical Analyses
Pharmacokinetics of Oxymorphone and Metabolites in Plasma The average plasma concentrations over time are shown in FIG. 11. The average plasma concentrations of oxymorphone, 6-OH-oxymorphone, and oxymorphone-3-glucuronide followed a similar time course and the curves are

TABLE 33

Mean (SD) Plasma Pharmacokinetic Results (untransformed)

| Analyte/Variable | Mild Impairment | Moderate Impairment | Severe Impairment | Healthy Controls |
|---|---|---|---|---|
| *Oxymorphone* | | | | |
| AUC (ng · hr/mL) | 21.68 (5.07) | 27.93 (8.34) | 32.46 (19.12) | 18.86 (9.39) |
| AUCT (ng · hr/mL) | 19.00 (6.26) | 26.09 (8.01) | 29.72 (17.35) | 15.79 (9.46) |
| Cmax (ng/mL) | 1.47 (0.54) | 1.75 (0.59) | 2.04 (1.07) | 1.16 (0.71) |
| Tmax (hr)* | 3.5 (1.0-12.0) | 2.0 (0.5-5.0) | 2.0 (1.0-8.0) | 3.5 (0.5-12.0) |
| CLo (L/min.) | 16.14 (3.94) | 13.53 (6.52) | 13.79 (7.29) | 22.07 (10.56) |
| Ke (1/hr) | 0.0660 (0.0300) | 0.0733 (0.0162) | 0.0652 (0.0234) | 0.0544 (0.0135) |
| t½ (hr) | 12.42 (5.10) | 9.92 (2.45) | 13.35 (9.45) | 13.46 (3.38) |
| *6-OH-oxymorphone* | | | | |
| AUC (ng · hr/mL) | 18.57 (6.91) | 17.64 (6.12) | 32.04 (23.82) | 19.76 (11.17) |
| AUCT (ng · hr/mL) | 14.26 (4.39) | 11.70 (6.09) | 26.48 (21.36) | 14.95 (10.58) |
| Cmax (ng/mL) | 0.99 (0.30) | 0.76 (0.31) | 0.99 (0.55) | 0.70 (0.34) |
| Tmax (hr)* | 1.5 (1.0-4.0) | 2.5 (0.5-5.0) | 2.0 (1.0-4.0) | 1.5 (0.5-18.0) |
| Ke (1/hr) | 0.0451 (0.0148) | 0.0312 (0.0151) | 0.0349 (0.0199) | 0.0449 (0.0344) |
| t½ (hr) | 18.04 (9.92) | 27.82 (14.10) | 26.53 (13.91) | 22.20 (10.76) |
| *Oxymorphone-3-glucuronide* | | | | |
| AUC (ng · hr/mL) | 4468.6 (1352.0) | 8129.7 (3674.8) | 23604.2 (11675.3) | 2439.7 (597.7) |
| AUCT (ng · hr/mL) | 4330.7 (1334.7) | 7959.9 (3563.1) | 22313.6 (9560.2) | 2309.5 (532.6) |
| Cmax (ng/mL) | 280.2 (86.2) | 359.7 (156.0) | 547.7 (138.8) | 170.1 (21.7) |
| Tmax (hr)* | 3.5 (2.0-6.0) | 4.5 (2.0-12.0) | 11.0 (5.0-24.0) | 3.0 (2.0-5.0) |
| Ke (1/hr) | 0.0694 (0.0118) | 0.0657 (0.0148) | 0.0350 (0.0110) | 0.0770 (0.0218) |
| t½ (hr) | 10.23 (1.64) | 11.10 (2.87) | 22.09 (8.98) | 9.53 (2.16) |

Source: Appendix 2.13
*median (range)

The subjects with renal impairment had higher mean oxymorphone AUC and $C_{max}$ values than the healthy controls (Table 33). The mean oxymorphone AUC ranged from 18.86 to 34.46 ng·hr/mL and $C_{max}$ range from 1.16 to 2.04 ng/mL in healthy controls and subjects with severe renal impairment, respectively. There do not appear to be any substantial differences in median $T_{max}$ or in the mean elimination rate constants for oxymorphone. Mean elimination half-life ranged from 9.92 hours in subjects with moderate impairment to 13.46 hours in healthy controls.

Mean oxymorphone-3-glucuronide AUC and $C_{max}$ results were substantially higher in subjects with renal impairment relative to the healthy controls. The mean oxymorphone-3-glucuronide AUC ranged from 2440 to 23604 ng·hr/mL and $C_{max}$ range from 170 to 548 ng/mL in healthy controls and subjects with severe renal impairment, respectively. The differences in AUC and $C_{max}$ also seemed to be associated with a decrease in elimination rate. The mean elimination half-life for oxymorphone-3-glucuronide increased from 9.5 hours in healthy controls to 22.1 hours in subjects with severe renal impairment.

Pharmacokinetic differences between treatment groups are less clear for 6-OH-oxymorphone. While subjects with severe renal impairment had higher mean AUC values than healthy controls (32.04 vs. 19.76 ng·hr/mL, respectively), the mean AUC values in subjects with mild impairment (18.57 ng·hr/mL) and moderate impairment (17.64 ng·hr/mL) were lower than the controls.

The pharmacokinetic results for oxymorphone, 6-OH-oxymorphone, and oxymorphone-3-glucuronide were compared between treatment groups following ln-transformation (natural log). The AUC and Cmax results are shown in FIG. 12.

The mean bioavailability ratios (90% confidence intervals) for oxymorphone AUC are 1.2559 (0.8566-1.8414), 1.5722 (1.0723-2.3051), and 1.6529 (1.1274-2.4234) relative to controls in subjects with mild, moderate, and severe renal impairment, respectively. The mean bioavailability ratios (90% confidence intervals) for oxymorphone $C_{max}$ are 1.3772 (0.9359-2.0265), 1.6494 (1.1209-2.4270), and 1.8042 (1.2261-2.6549) relative to controls in subjects with mild, moderate, and severe renal impairment, respectively. As noted in FIG. 12, the lower 90% confidence limits for AUC and $C_{max}$ in subjects with mild renal impairment overlap 1.0, indicating that the observed differences were not statistically significant. The analysis of elimination rate constants also did not reveal any significant differences between subjects with renal impairment relative to healthy controls. In fact, the mean plasma oxymorphone elimination rate constants in subjects with renal impairment were higher than those in control subjects.

Figure 12:
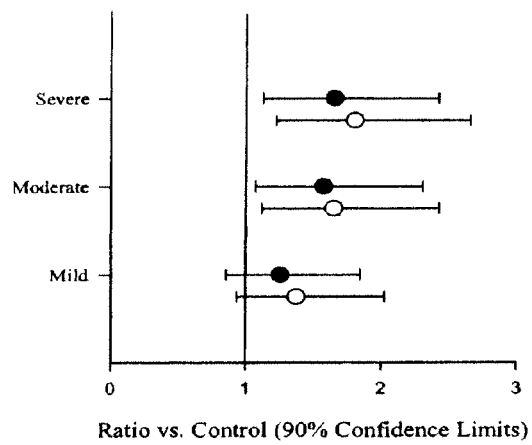
FIG. 12 is a graph of the ratio and 90% confidence limits for comparison of renally impaired to healthy controls (ln-transformed results).
Figure 12:
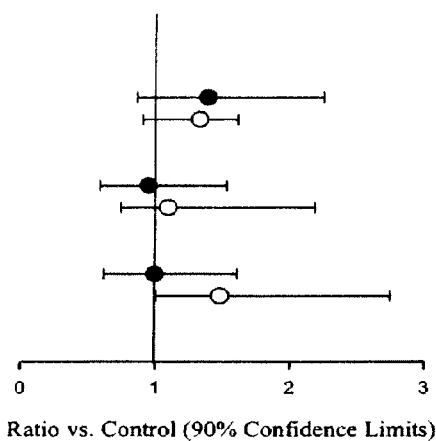
Figure 12:
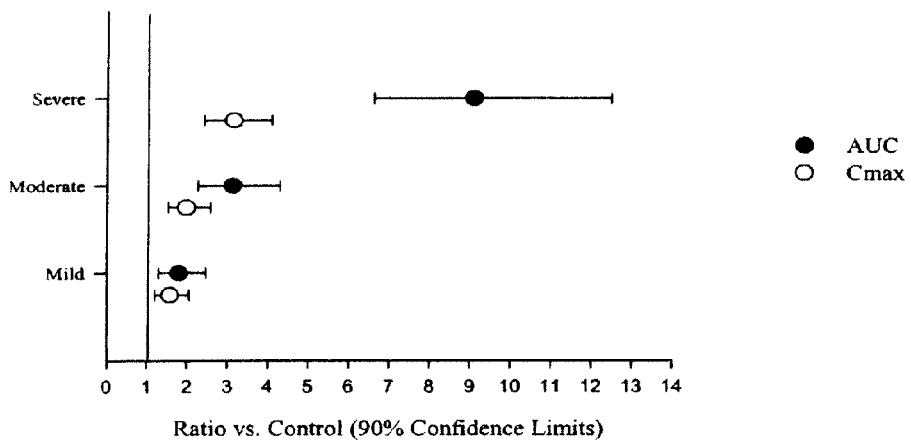

There were no statistically significant differences in mean AUC for 6-OH-oxymorphone in subjects with mild, moderate, or severe renal impairment relative to controls (FIG. 12). While the mean $C_{max}$ was significantly higher than controls in subjects with mild renal impairment (1.4818, 1.0067-2.1813), the relative bioavailability ratios were lower in subjects with moderate or severe renal impairment.

The mean bioavailability ratios (90% confidence intervals) for 6-OH-oxymorphone AUC are 0.9953 (0.6153-1.6100), 0.9445 (0.5839-1.5279), and 1.3862 (0.8569-2.2423) relative to controls in subjects with mild, moderate, and severe renal impairment, respectively.

The mean bioavailability ratios (90% confidence intervals) for oxymorphone-3-glucuronide Cmax are 1.5769 (1.2146-2.0473), 1.9830 (1.5274-2.5745), and 3.1422 (2.4202-4.0795) relative to controls in subjects with mild, moderate, and severe renal impairment, respectively.

After conversion to molar units, the ratio of AUC values for 6-OH-oxymorphone:oxymorphone and oxymorphone-3-glucuronide:oxymorphone were calculated. The results are shown in FIG. 13.

Figure 13:
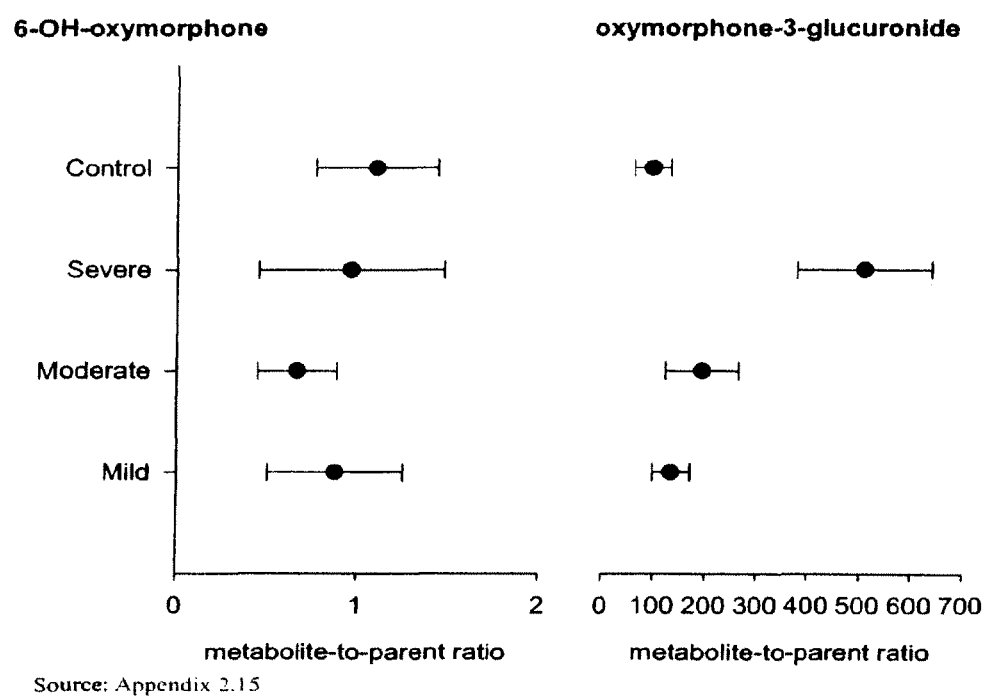
FIG. 13 is a graph of the mean (SD) plasma metabolite-to-parent ratios.

Examination of FIG. 13 indicates a significant degree of overlap between the four treatment groups for the ratio of 6-OH-oxymorphone:oxymorphone. The mean oxymorphone-3-glucuronide:oxymorphone ratios were 94.1, 132.3, 191.4, and 505.6 in healthy controls and subjects with mild, moderate, and severe renal impairment, respectively.

Pharmacokinetics of Oxymorphone and Metabolites in Urine

Figure 14:
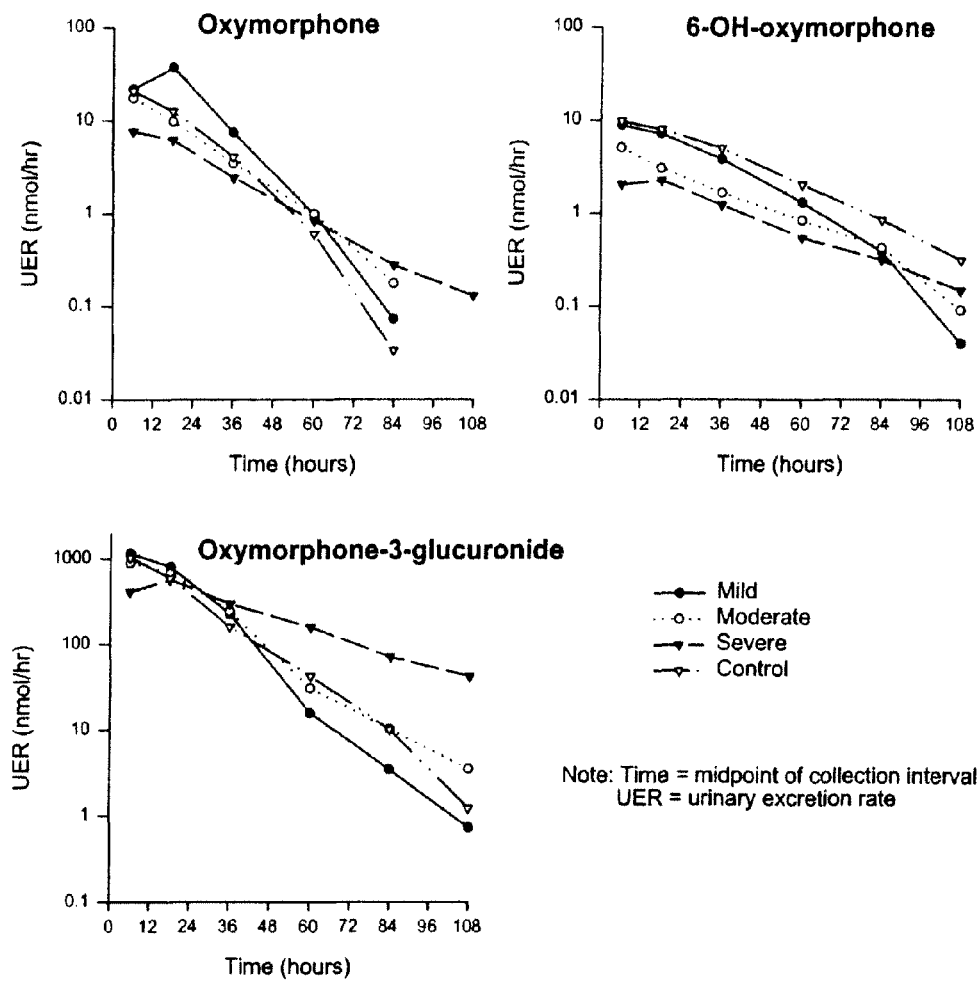
FIG. 14 is a graph of the mean urinary excretion rate (nmol/hr) of oxymorphone and metabolites.

Mean urinary excretion rates are plotted in FIG. 14. Urinary excretion of unchanged oxymorphone was essentially complete by the end of the 72 to 96 hour collection interval for healthy controls and subjects with mild or moderate renal impairment. Examination of the urinary excretion rate plots (FIG. 14) indicates essentially parallel excretion rate curves for oxymorphone in healthy controls and subjects with mild or moderate renal impairment; subjects with severe renal impairment excreted oxymorphone at a slower rate. Mean urinary elimination half-lives for oxymorphone were 12.5, 12.1, 13.9, and 21.0 hours in healthy controls and subjects with mild, moderate, and severe renal impairment, respectively.

Similar patterns of urinary excretion were observed for the 6-OH and 3-glucuronide metabolites (FIG. 14); healthy controls and subjects with mild or moderate renal impairment had similar rates of excretion for the two metabolites, but subjects with severe renal impairment excreted the metabolites at a slower rate. Mean urinary elimination half-lives for 6-OH-oxymorphone were 22.8, 19.6, 22.4, and 34.4 hours in healthy controls and subjects with mild, moderate, and severe renal impairment, respectively. Mean urinary elimination half-lives for oxymorphone-3-glucuronide were 12.7, 9.8, 12.8, and 36.6 hours in healthy controls and subjects with mild, moderate, and severe renal impairment, respectively.

Figure 15:
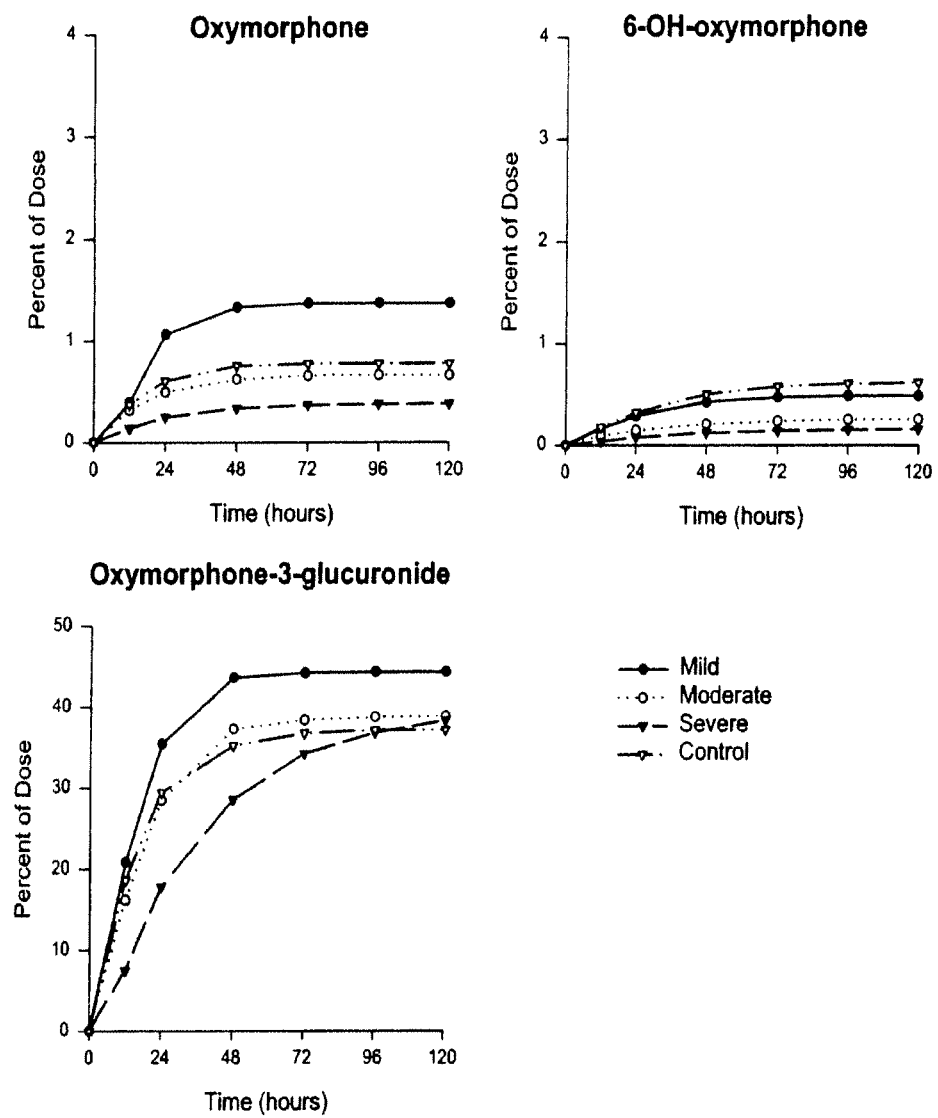
FIG. 15 is a graph of the cumulative urinary excretion of oxymorphone and metabolites (percent of administered dose).

The cumulative amounts of oxymorphone, 6-OH-oxymorphone, and oxymorphone-3-glucuronide excreted in the urine are shown in FIG. 15, and the total amounts of oxymorphone and its metabolites recovered in the urine are summarized in Table 34.

In all four treatment groups, urinary recovery of oxymorphone and 6-OH-oxymorphone was greatest in the first 24 hours following dose administration and was nearly complete by the end of the 48 hour collection interval (FIG. 5). The mean amount oxymorphone excreted unchanged in the urine ranged from 0.38%-1.37% of the administered dose in subjects with severe and mild renal impairment, respectively (Table 34). The mean percentage of the administered dose excreted in the urine as 6-OH-oxymorphone ranged from 0.16%-0.62% in subjects with severe renal impairment and healthy controls, respectively. Consistent with the lower mean urinary excretion rates, subjects with severe renal impairment excreted less oxymorphone and 6-OH-oxymorphone in the urine than subjects in the other three treatment groups.

Oxymorphone-3-glucuronide was the primary urinary metabolite in all four treatment groups. The mean percentage of the administered dose excreted in the urine as oxymorphone-3-glucuronide ranged from 37.16%-44.36% in healthy controls and subjects with mild renal impairment, respectively (Table 34). While the recovery of oxymorphone-3-glucuronide was essentially complete by 48 hours in healthy controls and subjects with mild or moderate renal impairment, excretion of this metabolite in subjects with severe renal impairment lagged behind the other groups (FIG. 15). The total amount of oxymorphone-3-glucuronide recovered in the urine for subjects with severe renal impairment did not reach the levels seen in healthy controls until the end of the 96 hour collection interval.

TABLE 34

Total Percent of Dose Recovered in Urine (0-120 hours)

| | Mean (SD) Percent of Dose Recovered (0-120 hours) | | | |
|---|---|---|---|---|
| Compound | Mild | Moderate | Severe | Control |
| Oxymorphone | 1.37 (2.10) | 0.66 (0.29) | 0.38 (0.19) | 0.77 (0.36) |
| 6-OH-oxymorphone | 0.49 (0.15) | 0.26 (0.14) | 0.16 (0.11) | 0.62 (0.28) |
| Oxymorphone-3-glucuronide | 44.36 (8.72) | 38.87 (8.63) | 38.35 (13.10) | 37.16 (14.94) |

Source: Appendix 2.26

The mean ratios of the amount of metabolite excreted in the urine relative to the amount of unchanged oxymorphone excreted in the urine are summarized in Table 35.

TABLE 35

Mean (SD) Urinary Metabolite Ratios

| | Mean (SD) Ratio of Metabolite/Parent Excreted in Urine | | | |
|---|---|---|---|---|
| Compound | Mild | Moderate | Severe | Control |
| 6-OH-OXM:OXM | 0.73 (0.45) | 0.41 (0.22) | 0.47 (0.42) | 0.85 (0.27) |
| OXM-3-G:OXM | 72.17 (48.36) | 70.62 (37.69) | 112.44 (40.45) | 51.78 (16.89) |

6-OH-OXM = 6-OH-oxymorphone; OXM = oxymorphone, OXM-3-G = oxymorphone-3-glucuronide
Source: Appendix 2.25

The ratio of 6-OH-oxymorphone:oxymorphone excreted in the urine was reduced by approximately one-half in subjects with moderate or severe renal impairment relative to controls (Table 35), reflecting the reduction in urinary excretion of 6-OH-oxymorphone noted in Table 34. The large increase oxymorphone-3-glucuronide:oxymorphone ratio observed in patients with severe renal impairment primarily reflects the observed reduction in renal excretion of oxymorphone, since there is little difference in the total amount of oxymorphone-3-glucuronide excreted in the urine between subjects with severe renal impairment (38.35% of the dose) and controls (37.16% of the dose, Table 34).

Relationship between Oxymorphone Oral Clearance and Measures of Renal Function

Figure 16:
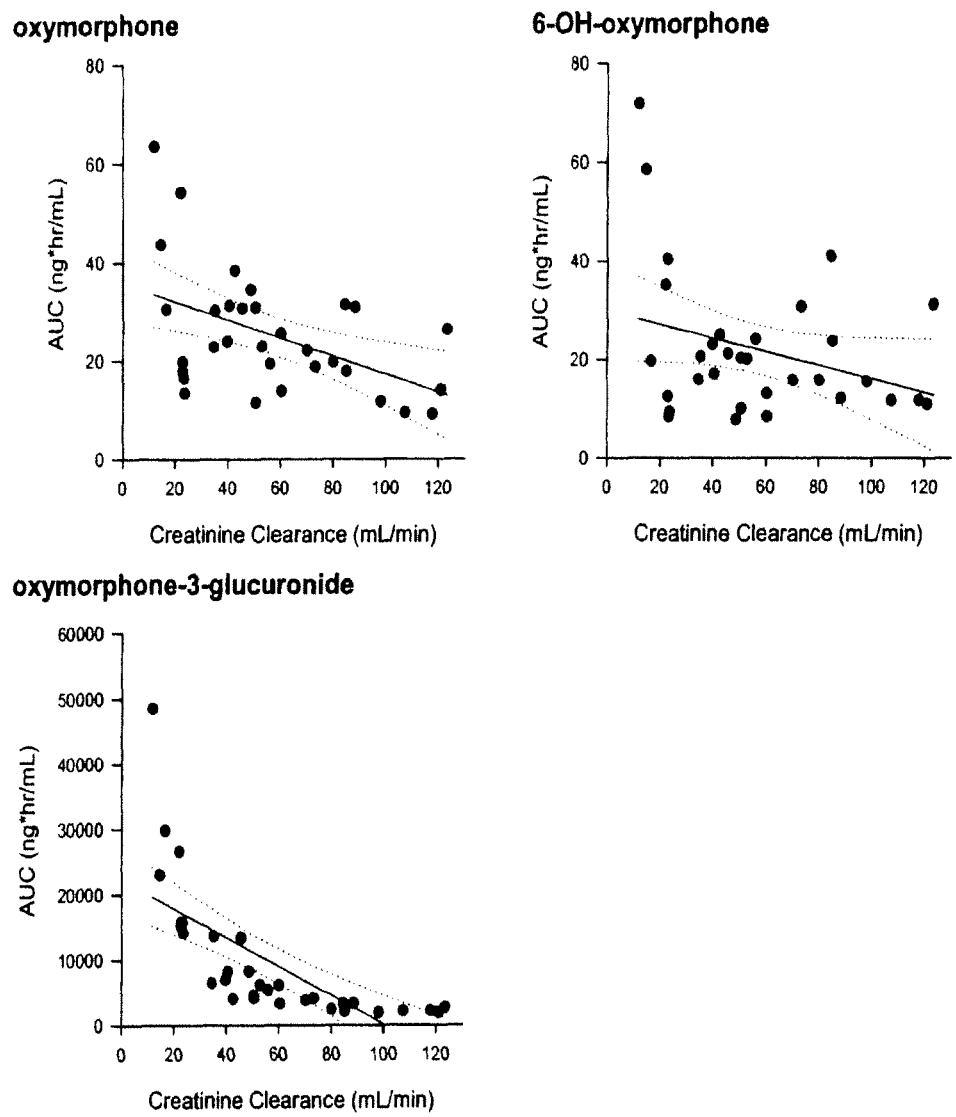
FIG. 16 is a graph of the relationship between AUC and creatinine clearance.

The potential association between plasma AUC and creatinine clearance was explored using linear regression techniques and the results are summarized in Table 36 and FIG. 16.

There was a weak positive association between oxymorphone oral clearance and creatinine clearance, that while statistically significant, explains very little of the observed variation (Table 36).

TABLE 36

Correlation of Oxymorphone and Metabolite
Plasma AUC with Creatinine Clearance

| Correlation | Slope | R-square | P-value |
|---|---|---|---|
| oxymorphone: CL/F vs. $CL_{CR}$ | 0.1229 | 0.2592 | 0.0029 |
| oxymorphone: AUC vs. $CL_{CR}$ | −0.1852 | 0.2400 | 0.0044 |
| 6-OH-oxymorphone: AUC vs. $CL_{CR}$ | −0.1387 | 0.0977 | 0.0815 |
| oxymorphone-3-glucuronide: AUC vs. $CL_{CR}$ | −221.43 | 0.4976 | 0.0000 |
| oxymorphone: AUC/wt vs. $CL_{CR}$ | −0.0013 | 0.2898 | 0.0015 |

TABLE 36-continued

Correlation of Oxymorphone and Metabolite
Plasma AUC with Creatinine Clearance

| Correlation | Slope | R-square | P-value |
|---|---|---|---|
| 6-OH-oxymorphone: AUC/wt vs. $CL_{CR}$ | −0.0011 | 0.1222 | 0.0499 |
| oxymorphone-3-glucuronide: AUC/wt vs. $CL_{CR}$ | −1.4140 | 0.4911 | 0.0000 |

$CL_{CR}$ = creatinine clearance
AUC/wt = AUC normalized for body weight

As noted in Table 36, the only meaningful association appears to be for oxymorphone-3-glucuronide AUC and creatinine clearance. Examination of FIG. 6, indicates that there is relatively little changes in AUC for the 3-glucuronide metabolite until creatinine clearance falls below 50 mL/min. For all three analytes, the most extreme values tend to be observed when creatinine clearance is <30 mL/min.

Safety

Extent of Exposure

A total of 34 subjects received a single, oral, 20-mg dose of EN3202. The trial included 9 subjects with mild renal impairment, 8 subjects with moderate renal impairment, 9 subjects with severe renal impairment, and 8 healthy controls. Thirty-two (32) subjects completed the trial; 2 subjects (1 with mild and 1 with severe renal impairment) discontinued the trial due to adverse experiences. All 34 subjects also received a single oral dose of naltrexone (50 mg) administered during the evening prior to administration of the EN3202 dose.

Adverse Events

Twenty-five (25) subjects with renal impairment and three (3) healthy control subjects reported one or more adverse experiences (TABLE 37).

TABLE 37

Summary of Adverse Experiences (Event Reported by Two or More Subjects)

|  | Mild Impairment | Moderate Impairment | Severe Impairment | Healthy Controls |
|---|---|---|---|---|
| Total Number of Subjects | 9 | 8 | 9 | 8 |
| Number with at least one AE | 9 (100.0%) | 7 (87.5%) | 9 (100.0%) | 3 (37.5%) |
| Headache NOS | 5 (55.6%) | 3 (37.5%) | 3 (33.3%) | 2 (25.0%) |
| Nausea | 4 (44.4%) | 0 | 4 (44.4%) | 0 |
| Feeling of Relaxation | 5 (55.6%) | 0 | 2 (22.2%) | 0 |
| Dizziness (exc vertigo) | 1 (11.1%) | 0 | 3 (33.3%) | 1 (12.5%) |
| Back Pain | 2 (22.2%) | 0 | 2 (22.2%) | 0 |
| Constipation | 2 (22.2%) | 1 (12.5%) | 1 (11.1%) | 0 |
| Vomiting NOS | 3 (33.3%) | 0 | 1 (11.1%) | 0 |
| Arthralgia | 1 (11.1%) | 2 (25.0%) | 0 | 0 |
| Euphoric Mood | 2 (22.2%) | 0 | 0 | 1 (12.5%) |
| Abdominal Pain NOS | 1 (11.1%) | 0 | 1 (11.1%) | 0 |
| Dyspepsia | 1 (11.1%) | 1 (12.5%) | 0 | 0 |
| Feeling Hot | 2 (22.2%) | 0 | 0 | 0 |
| Hypertension NOS | 0 | 0 | 2 (22.2%) | 0 |
| Rigors | 1 (11.1%) | 0 | 1 (11.1%) | 0 |
| Somnolence | 0 | 0 | 2 (22.2%) | 0 |

The majority of adverse experiences were mild in severity and occurred primarily in subjects with renal impairment. None of the moderate or severe adverse experiences occurred in the healthy control or moderate renal impairment subject group. Four moderate adverse experiences occurred in subjects with mild renal impairment; five moderate adverse experiences and one severe adverse experience occurred in subjects with severe renal impairment. The only severe adverse experience was back pain.

Clinical Laboratory

Clinical laboratory tests were obtained at screening and at the end of the inpatient observation period (Day 5). One subject (305—severe renal impairment group) had a clinically significant decline in renal function during the trial. Serum creatinine increased from 5.6 mg/dL at baseline to 7.9 mg/dL at end of the trial; BUN was essentially unchanged (74 mg/dL at baseline and 92 mg/dL at end of study). This subject had nausea and vomiting shortly after dose administration and was removed from the study due to the close proximity between the episode of vomiting and the time of dose administration (in accordance with the study protocol). The subject remained in the clinic overnight and was discharged. The subject was contacted by the investigator to see his regular physician for follow-up when the laboratory results were obtained. Follow-up results revealed a serum creatinine of 6.0 mg/dL and BUN of 88 mg/dL.

A total of 25 subjects had one or more serum chemistry values outside the reference range at the end of the study evaluation. Except as noted above, the observed changes were small and not clinically significant.

A total of 30 subjects had one or more hematology parameters outside the reference range at the end of the study evaluation. Most of the observed changes were small, and none were clinically significant.

Vital Signs

Vital signs, including pulse, respiratory rate, blood pressure, and temperature, were obtained during the screening physical examination, just prior to administration of the test medication, and at 24, 48, 72, 96, and 120 hours after administration of the test medication.

No clinically significant changes were observed in pulse, respiratory rate, blood pressure, or temperature. Subject 300 (a 66 year old male with severe renal impairment who was previously treated for hypertension) had a blood pressure rate of 140/88 at screening. During the trial, his blood pressure fluctuated between 190/98 and 220/110. No meaningful trends emerged during the 120 hour treatment period.

Physical Examination and ECG

Medical history data were collected at screening. Physical examinations were performed at screening and at the end of the study. No clinically significant findings were found. A 12-lead ECG was performed at screening. No clinically significant readings were recorded.

Concomitant Medication

One healthy control subject was on birth control medication. A total of 25 subjects out of 26 subjects with renal impairment received one or more concomitant medications. Twenty-one (21) of the subjects with renal impairment received medication for hypertension, ten (10) for diabetes, and eight (8) for renal conditions. The most common concomitant medications administered were insulin for diabetes, lisinopril for hypertension, and furosemide for hypertension and renal conditions.

Summary of Analytical Performance

The study clinic shipped plasma and urine samples to the analytical site. The performance of the analytical methods during this period is summarized in the following tables.

TABLE 38

Summary of Analytical Performance for Plasma Analytes

| Parameter | OXM | 6-OH-OXM | OXM-3-G |
|---|---|---|---|
| Number of Runs | 12 | 12 | 13 |
| Linearity (mean r) | 0.998 | 0.998 | 0.999 |
| Inter-day Precision (% CV)* | 4.49-7.86% | 5.73-10.00% | 2.79-6.12% |
| Inter-day Accuracy (% Actual)* | −5.08--4.57% | −4.31--1.76% | −1.90-0.07% |

*precision and accuracy results based on QC samples excluding dilutions
OXM = oxymorphone
6-OH-OXM = 6-OH-oxymoiphone
OXM-3-G = oxymorphone-3-glucuronide

TABLE 39

Summary of Analytical Performance for Urine Analytes

| Parameter | OXM | 6-OH-OXM | OXM-3-G |
|---|---|---|---|
| Number of Runs | 4 | 3 | 2 |
| Linearity (mean r) | 0.999 | 0.999 | 0.997 |
| Inter-day Precision (% CV)* | 2.73-5.12% | 4.41-6.49% | 0.42-4.94% |

TABLE 39-continued

Summary of Analytical Performance for Urine Analytes

| Parameter | OXM | 6-OH-OXM | OXM-3-G |
|---|---|---|---|
| Inter-day Accuracy (% Actual)* | −4.42-1.30% | −4.13--0.24% | −6.85-9.23% |

*precision and accuracy results based on QC samples excluding dilutions
OXM = oxymorphone
6-OH-OXM = 6-OH-oxymorphone
OXM-3-G = oxymorphone-3-glucuronide Discussion The mean bioavailability ratios (90% confidence intervals) for oxymorphone AUC are 1.2559 (0.8566-1.8414), 1.5722 (1.0723-2.3051), and 1.6529 (1.1274-2.4234) relative to controls in subjects with mild, moderate, and severe renal impairment, respectively. There were no statistically significant differences in mean AUC for 6-OH-oxymorphone in subjects with mild, moderate, or severe renal impairment relative to controls. The mean bioavailability ratios (90% confidence intervals) for oxymorphone-3-glucuronide AUC are 1.7960 (1.3071-2.4677), 3.1196 (2.2704-4.2863), and 9.0701 (6.6013-12.462) relative to controls in subjects with mild, moderate, and severe renal impairment, respectively.

The log(natural log or ln) transformed AUC of oxymorphone of a patient with moderately impaired kidney function may be about 1.05 to about 2.35 times greater than that of a healthy patient, for example about 1.05 times greater, about 1.10 times greater, about 1.15 times greater, about 1.20 times greater, about 1.25 times greater, about 1.30 times greater, about 1.35 times greater, about 1.40 times greater, about 1.45 times greater, about 1.50 times greater, about 1.55 times greater, about 1.60 times greater, about 1.65 times greater, about 1.70 times greater, about 1.75 times greater, about 1.80 times greater, about 1.85 times greater, about 1.90 times greater, about 1.95 times greater, about 2.00 times greater, about 2.05 times greater, about 2.10 times greater, about 2.15 times greater, about 2.20 times greater, about 2.25 times greater, about 2.30 times greater, or about 2.35 times greater.

The log (natural log or ln) transformed AUC of oxymorphone of a patient with severely impaired kidney function may be about 1.10 to about 2.45 times greater than that of a healthy patient, for example about 1.10 times greater, about 1.15 times greater, about 1.20 times greater, about 1.25 times greater, about 1.30 times greater, about 1.35 times greater, about 1.40 times greater, about 1.45 times greater, about 1.50 times greater, about 1.55 times greater, about 1.60 times greater, about 1.65 times greater, about 1.70 times greater, about 1.75 times greater, about 1.80 times greater, about 1.85 times greater, about 1.90 times greater, about 1.95 times greater, about 2.00 times greater, about 2.05 times greater, about 2.10 times greater, about 2.15 times greater, about 2.20 times greater, about 2.25 times greater, about 2.30 times greater, about 2.35 times greater, about 2.40 times greater, or about 2.45 times greater.

The log (natural log or ln) transformed $C_{max}$ of oxymorphone of a patient with moderately impaired kidney function may be about 1.10 to about 2.45 times greater than that of a healthy patient, for example about 1.10 times greater, about 1.15 times greater, about 1.20 times greater, about 1.25 times greater, about 1.30 times greater, about 1.35 times greater, about 1.40 times greater, about 1.45 times greater, about 1.50 times greater, about 1.55 times greater, about 1.60 times greater, about 1.65 times greater, about 1.70 times greater, about 1.75 times greater, about 1.80 times greater, about 1.85 times greater, about 1.90 times greater, about 1.95 times greater, about 2.00 times greater, about 2.05 times greater, about 2.10 times greater, about 2.15 times greater, about 2.20 times greater, about 2.25 times greater, about 2.30 times greater, about 2.35 times greater, about 2.40 times greater, or about 2.45 times greater.

The log (natural log or ln) transformed $C_{max}$ of oxymorphone of a patient with severely impaired kidney function may be about 1.20 to about 2.70 times greater than that of a healthy patient, for example about 1.20 times greater, about 1.25 times greater, about 1.30 times greater, about 1.35 times greater, about 1.40 times greater, about 1.45 times greater, about 1.50 times greater, about 1.55 times greater, about 1.60 times greater, about 1.65 times greater, about 1.70 times greater, about 1.75 times greater, about 1.80 times greater, about 1.85 times greater, about 1.90 times greater, about 1.95 times greater, about 2.00 times greater, about 2.05 times greater, about 2.10 times greater, about 2.15 times greater, about 2.20 times greater, about 2.25 times greater, about 2.30 times greater, about 2.35 times greater, about 2.40 times greater, about 2.45 times greater, about 2.50 times greater, about 2.55 times greater, about 2.60 times greater, about 2.65 times greater, or about 2.70 times greater.

All of the changes in plasma concentrations were accompanied by reductions in urinary excretion rates of percentage of the dose excreted in the urine. For example, the mean oxymorphone AUC was increased by an average of 1.7-fold and the mean percentage of the dose excreted in the urine as unchanged oxymorphone was reduced by approximately 50% in subjects with severe renal impairment relative to healthy controls. Decreasing levels of renal function had a greater effect on the circulating concentrations of oxymorphone-3-glucuronide than on the plasma levels of oxymorphone. This is not unexpected since the 3-glucuronide metabolite is the primary metabolite found in the urine. The mean urinary excretion rate half-life was 36.6 hours in subjects with severe renal impairment and 12.7 hours in healthy controls.

There were weak, but statistically significant correlations between plasma AUC for oxymorphone and oxymorphone-3-glucuronide and creatinine clearance. The small $r^2$ values appear to be related, at least in part, to the fact that the relationship is not entirely linear. There is relatively little change in plasma AUC for either oxymorphone or oxymorphone-3-glucuronide until the creatinine clearance falls below 50 mL/min; and the highest AUC values were observed in subjects with creatinine clearance values <30 mL/min.

CONCLUSION

Moderate-to-severe renal insufficiency was associated with a reduction in the renal excretion of oxymorphone and its principal urinary metabolite, oxymorphone-3-glucuronide. These changes were associated with mean increases in plasma AUC values relative to healthy controls of approximately 1.8-fold and 9.7-fold for oxymorphone and oxymorphone-3-glucuronide, respectively in subjects with creatinine clearance values, 30 mL/min.

All references, including publications, patent applications, and patents, cited herein are hereby incorporated by reference to the same extent as if each reference there individually and specifically indicated to be incorporated by reference were set forth in its entirety herein.

The use of the terms "a" and "an" and "the" and similar referents in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the invention.

Alternative embodiments of the claimed invention are described herein, including the best mode known to the inventors for carrying out the claimed invention. Of these, variations of the disclosed embodiments will become apparent to those of ordinary skill in the art upon reading the foregoing disclosure. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the claimed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value. Thus, as a general matter, "about" or "approximately" broaden the numerical value. Also, the disclosure of ranges is intended as a continuous range including every value between the minimum and maximum values plus the broadening of the range afforded by the use of the term "about" or "approximately". Thus, recitation of ranges of values herein are merely intended to serve as a shorthand method of referring individually to each separate value falling within the range, unless otherwise indicated herein, and each separate value is incorporated into the specification as if it were individually recited herein.

What is claimed is:

1. A method of treating pain in a renally impaired patient, comprising the steps of:
   a. providing a solid oral controlled release dosage form, comprising:
      i. about 5 mg to about 80 mg of oxymorphone or a pharmaceutically acceptable salt thereof as the sole active ingredient; and
      ii. a controlled release matrix;
   b. measuring a creatinine clearance rate of the patient and determining it to be (a) less than about 30 ml/min, (b) about 30 mL/min to about 50 mL/min, (c) about 51 mL/min to about 80 mL/min, or (d) above about 80 mL/min; and
   c. orally administering to said patient, in dependence on which creatinine clearance rate is found, a lower dosage of the dosage form to provide pain relief;
   wherein after said administration to said patient, the average AUC of oxymorphone over a 12-hour period is less than about 21 ng·hr/mL.

2. The method of claim 1, wherein the average AUC of oxymorphone over a 12-hour period is less than about 20 ng·hr/mL.

3. The method of claim 1, wherein the average AUC of oxymorphone over a 12-hour period is less than about 19 ng·hr/mL.

4. A method of treating pain in a renally impaired patient, comprising the steps of:
   a. providing a solid oral controlled release dosage form, comprising:
      i. about 5 mg to about 80 mg of oxymorphone or a pharmaceutically acceptable salt thereof as the sole active ingredient; and
      ii. a controlled release matrix;
   b. measuring a creatinine clearance rate of the patient and determining it to be (a) less than about 30 mL/min, (b) about 30 mL/min to about 50 mL/min, (c) about 51 mL/min to about 80 mL/min, or (d) above about 80 ml/min; and
   c. orally administering to said patient, in dependence on which creatinine clearance rate is found, a lower dosage of the dosage form to provide pain relief;
   wherein after said administration to said patient, the Cmax of oxymorphone is less than about 1.4 ng/mL.

5. The method of claim 4, wherein the average Cmax of oxymorphone is less than about 1.3 ng/mL.

6. The method of claim 4, wherein the average Cmax of oxymorphone is less than about 1.2 ng/mL.

* * * * *

UNITED STATES PATENT AND TRADEMARK OFFICE
CERTIFICATE OF CORRECTION

PATENT NO. : 8,808,737 B2  Page 1 of 1
APPLICATION NO. : 12/716973
DATED : August 19, 2014
INVENTOR(S) : Harry Ahdieh It is certified that error appears in the above-identified patent and that said Letters Patent is hereby corrected as shown below:

In the Specification

- Column 18, line 62, in Table 14, "7.768" should read "0.768".

- Column 19, line 27, in Table 16, "$F_{rel}$ (3A vs. 2C)" should read "$F_{rel}$ (3A vs. 3C)".

In the Claims

- Column 48, line 16, in Claim 1, "30 ml/min" should read "30 mL/min".

- Column 48, line 44, in Claim 4, "ml/min" should read "mL/min".

Signed and Sealed this
Fourteenth Day of April, 2015

Michelle K. Lee
*Director of the United States Patent and Trademark Office*